United States Patent
Chang et al.

(10) Patent No.: US 12,403,121 B2
(45) Date of Patent: Sep. 2, 2025

(54) ANTICANCER ROCAGLAMIDE DERIVATIVES

(71) Applicant: The Research Institute at Nationwide Children's Hospital, Columbus, OH (US)

(72) Inventors: Long-Sheng Chang, Hilliard, OH (US); A. Douglas Kinghorn, Columbus, OH (US)

(73) Assignee: The Research Institute at Nationwide Children's Hospital, Columbus, OH (US)

( * ) Notice: Subject to any disclaimer, the term of this patent is extended or adjusted under 35 U.S.C. 154(b) by 797 days.

(21) Appl. No.: 17/284,112

(22) PCT Filed: Oct. 9, 2019

(86) PCT No.: PCT/US2019/055304
§ 371 (c)(1),
(2) Date: Apr. 9, 2021

(87) PCT Pub. No.: WO2020/076889
PCT Pub. Date: Apr. 16, 2020

(65) Prior Publication Data
US 2021/0346337 A1  Nov. 11, 2021

Related U.S. Application Data

(60) Provisional application No. 62/743,230, filed on Oct. 9, 2018.

(51) Int. Cl.
 *A61K 31/343* (2006.01)
 *A61K 9/00* (2006.01)
 *A61P 35/00* (2006.01)

(52) U.S. Cl.
 CPC .......... *A61K 31/343* (2013.01); *A61K 9/0019* (2013.01); *A61K 9/0053* (2013.01); *A61P 35/00* (2018.01)

(58) Field of Classification Search
 CPC ............................ A61K 31/343; A61K 9/0053
 See application file for complete search history.

(56) References Cited

U.S. PATENT DOCUMENTS

2016/0287553 A1* 10/2016 Becker .................. A61K 45/06
2017/0137400 A1*  5/2017 Marion ................ C07D 498/04

FOREIGN PATENT DOCUMENTS

| EP | 2189158 A1 | 5/2010 |
|---|---|---|
| WO | 2005/092876 A1 | 10/2005 |
| WO | 2016/207363 A1 | 12/2016 |
| WO | WO-2017040304 A1 * | 3/2017 ............ A61K 38/07 |

OTHER PUBLICATIONS

Bohnenstengel et al. Structure Activity Relationships of Antiproliferative Rocaglamide Derivatives from *Aglaia* Species (Meliaceae), (Julius-von-Sachs-Institute of Biosciences), Sep. 1999, pp. 55-60, [online], [retrieved on Nov. 27, 2023]. Retrieved from the internet <URL: https://www.degruyter.com (Year: 1999).*

Huang et al. NF1 Is a Tumor Suppressor in Neuroblastoma that Determines Retinoic Acid Response and Disease Outcome (Year: 2010).*

Huang et al. NF1 is a tumor suppressor in neuroblastoma that determines retinoic acid response and disease outcome, Cell, Jul. 2010, pp. 218-229. (Year: 2010).*

Bohnenstengel, Frank I., et al. "Structure activity relationships of antiproliferative rocaglamide derivatives from Aglaia species (Meliaceae)." Zeitschrift für Naturforschung C 54.1-2 (1999): 55-60.

Becker, Michael S., et al. "The anticancer phytochemical rocaglamide inhibits Rho GTPase activity and cancer cell migration." Oncotarget 7.32 (2016): 51908.

Yao, Chao, et al. "Rocaglamide enhances NK cell-mediated killing of non-small cell lung cancer cells by inhibiting autophagy." Autophagy 14.10 (2018): 1831-1844.

Applicant: The Research Institute at Nationwide Children's Hospital; "Anticancer Rocaglamide Derivatives"; International Application No. PCT/US2019/055304 Filed: Oct. 9, 2019; PCT International Search Report and Written Opinion dated Jan. 2, 2020; 46 pgs.

(Continued)

*Primary Examiner* — Sarah Pihonak
*Assistant Examiner* — Mikhail O'Donnel Robinson
(74) *Attorney, Agent, or Firm* — Tarolli, Sundheim, Covell & Tummino LLP

(57) ABSTRACT

A method of treating nervous system cancer or soft-tissue sarcoma in a subject is described. The method includes administering a therapeutically effective amount of a compound according to formula I to a subject in need thereof:

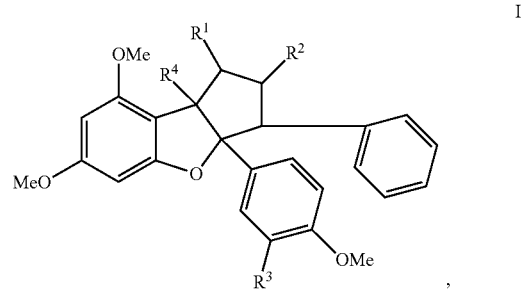

wherein $R^1$ is selected from the group consisting of —OH, —OAc, —OCHO, =O, and =NOH; $R^2$ is selected from the group consisting of —CON(CH$_3$)$_2$, —CONHCH$_3$, —CONH$_2$, —COOCH$_3$, —COOH, and —H, $R^3$ is selected from the group consisting of —H, —OH, and —OCH$_3$, and $R^4$ is selected from the group consisting of —OH, —OCH$_3$, —OCH$_2$CH$_3$.

13 Claims, 12 Drawing Sheets

(56) References Cited

OTHER PUBLICATIONS

Oblinger, Janet L.; Burns, Sarah S.; Akhmametyeva, Elena M.; Huang, Jie; Pan, Li; Ren, Yulin; Shen, Rulong; Miles-Markley, Beth; Moberly, Aaron C.; Kinghorn, A. Douglas; Welling, D. Bradley; Chang, Long-Sheng (2016). Components of the eIF4F complex are potential therapeutic targets for malignant peripheral nerve sheath tumors and vestibular schwannomas. Neuro-Oncology, (), now032-.doi: 10.1093/neuonc/now032.

Chu, J.; Cencic, R.; Wang, W.; Porco, J. A.; Pelletier, J. (2015). Translation Inhibition by Rocaglates Is Independent of eIF4E Phosphorylation Status. Molecular Cancer Therapeutics, (), 1535-7163.MCT-15-0409-. doi: 10. 1158/1535-7163.mct-15-0409.

Gupta, Sneha V., et al. "Resistance to the translation initiation inhibitor silvestrol is mediated by ABCB1/P-glycoprotein overexpression in acute lymphoblastic leukemia cells." The AAPS journal 13 (2011): 357-364.

Applicant: The Research Institute at Nationwide Children's Hospital; European Application No. 19870670.7-1109; European Office Action dated Jan. 20, 2025; 7 pgs.

\* cited by examiner

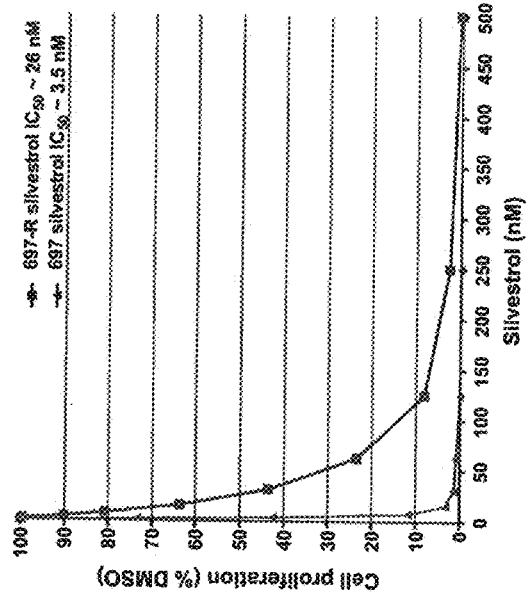
Figure 3A
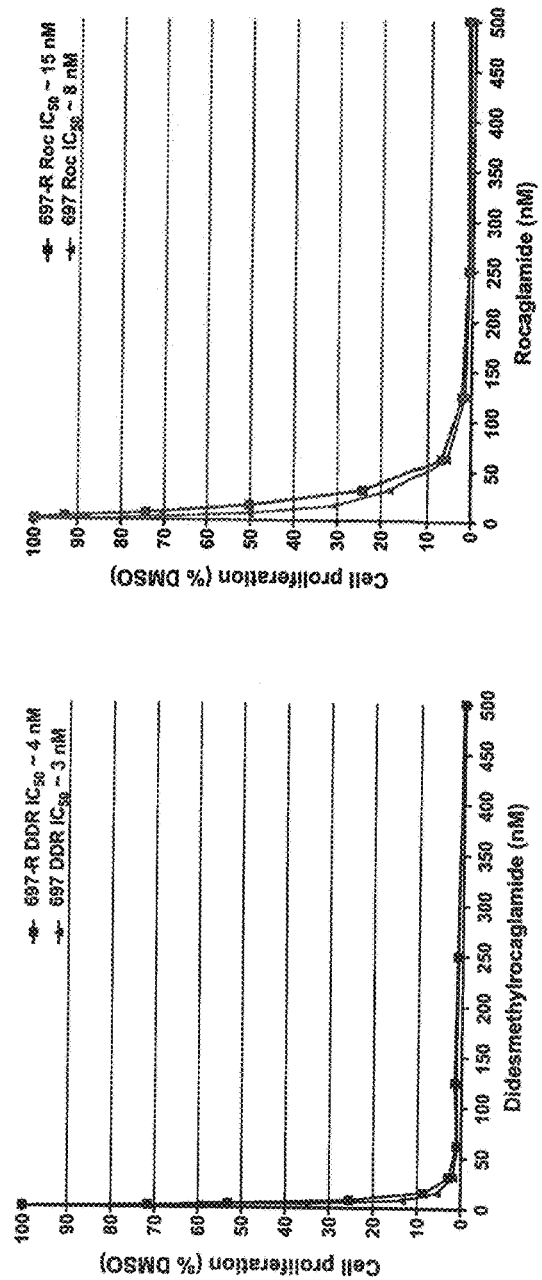
Figure 3B
Figure 3C

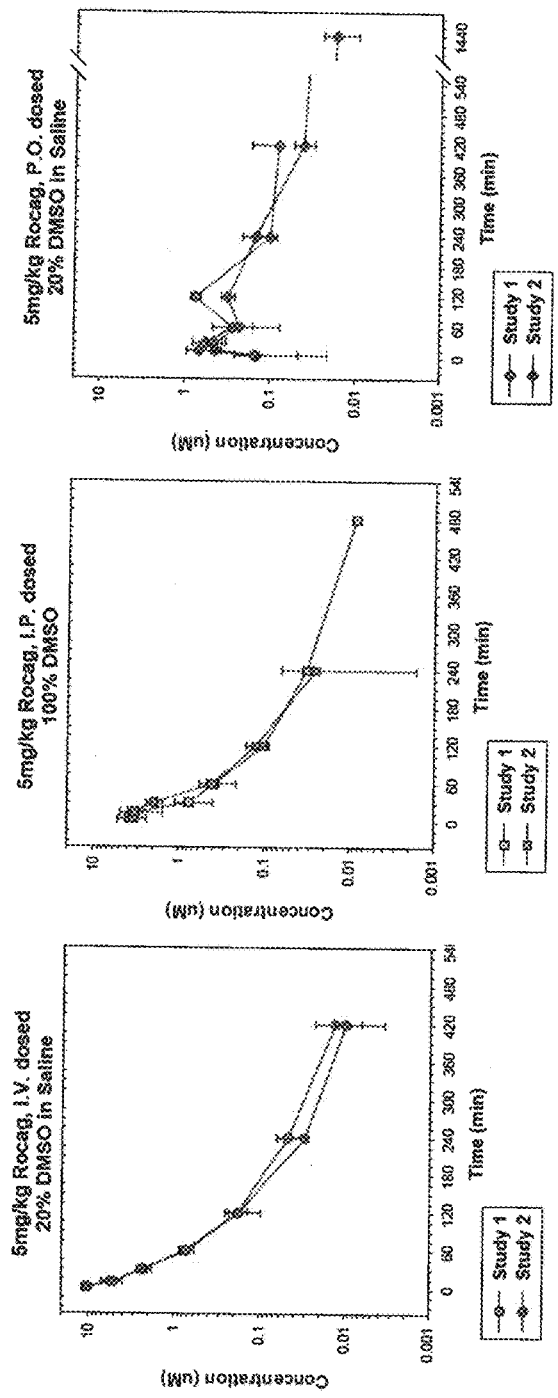
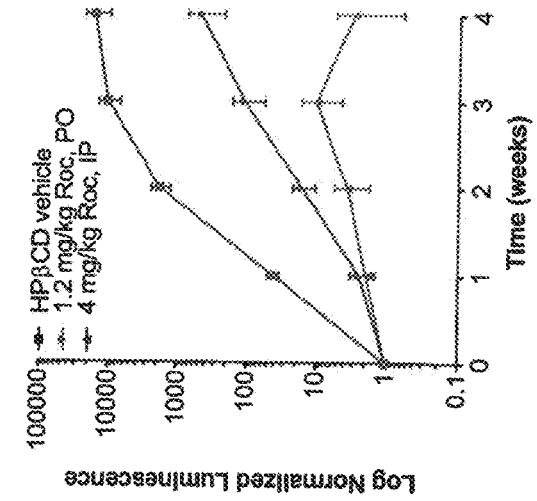
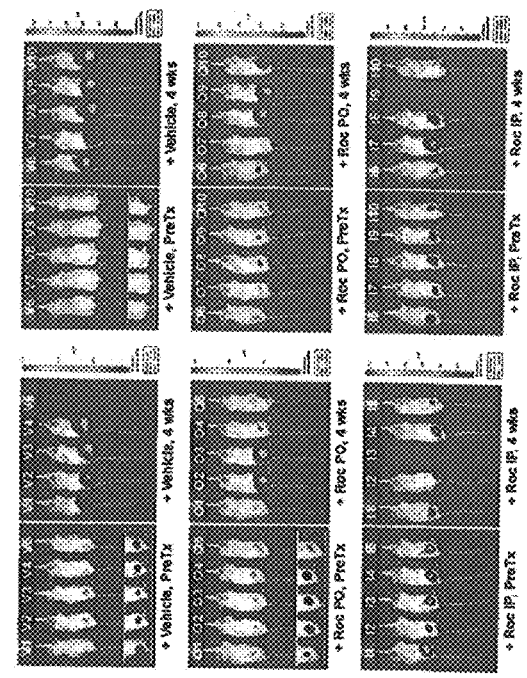
Figure 4A
Figure 4B
Figure 4C

ANTICANCER ROCAGLAMIDE DERIVATIVES

CROSS-REFERENCE TO RELATED APPLICATIONS

This application was a national stage application claiming the benefit of International Patent Application No. PCT/US2019/055304, filed on Oct. 9, 2019, which claims priority to U.S. Provisional Application No. 62/743,230, filed Oct. 9, 2018, both of which are incorporated by reference in their entirety.

GOVERNMENT FUNDING

This invention was made with government support under Grant No. CA125066 from the National Institutes of Health. The government has certain rights in the invention.

BACKGROUND

Malignant peripheral nerve sheath tumors (MPNSTs) are characterized as aggressive soft-tissue sarcomas with a high risk of recurrence and metastasis. Often refractory to current treatment, these tumors have a poor five-year survival rate of only about 20-50%. Higham et al., Sarcoma, 2017, U.S. Pat. No. 8,685,638 (2017). Therefore, development of more effective medical therapy that eradicate MPNSTs is of significant clinical need. MPNSTs can occur sporadically or arise from pre-existing plexiform neurofibromas in patients with neurofibromatosis type 1 (NF1), a tumor predisposition syndrome caused by mutations in the NF1 gene which encodes the Ras-GTPase-activating protein neurofibromin. Importantly, even sporadic tumors frequently harbor mutations in the NF1 gene or the Ras pathway. Consequently, both sporadic and NF1-associated MPNSTs exhibit upregulation of Ras downstream kinase signaling, including the phosphatidylinositol 3-kinase (PI3K)-AKT-mammalian target of rapamycin (mTOR) and Raf-MEK-ERK mitogen-activated protein kinases. MPNSTs also exhibit overexpression or aberrant activation of epidermal growth factor receptor (EGFR), platelet-derived growth factor receptor (PDGFR), and insulin-like growth factor-1 receptor (IGF-1R). Perrone et al., Neuro Oncol., 11:725-736 (2009). These reports suggest that these Ras downstream kinases and deregulated receptor tyrosine kinases (RTKs) may be therapeutic targets. Additionally, recurrent mutations in the tumor suppressor genes CDKN2A and TP53 and the subunits of the chromatin-modifying polycomb repressor complex-2 (PRC2), SUZ12 and EED, have been identified and are important for MPNST progression (Kim and Pratilas, Exp Neurol., 299(Pt B):317-325 (2018)). Inactivation of CDKN2A and TP53 disables the $G_1/S$ checkpoint. The loss of PRC2 function can lead to enhanced Ras-driven gene transcription (De Raedt et al., Nature, 514:247-512014).

As MPNSTs often exhibit hyperactive Ras activity, statins and farnesyl transferase inhibitors, which prevent localization of Ras to the membrane and inhibit MPNST cell growth (Barkan et al., Clin Cancer Res., 12:5533-5542 (2006)), have been evaluated but do not improve survival in patients with advanced cancer. Hanrahan et al., Am J Clin Oncol., 3:274-279 (2009). Drugs that target the deregulated RTKs and mitogenic kinases have also been investigated in patients with MPNSTs; however, the results have so far been disappointing. The EGFR inhibitor erlotinib elicited poor response rates in MPNSTs with only one of 20 patients exhibiting stable disease. Albritton et al., J Clin Oncol., 24:18(suppl): 9518 (2006). The IGF-1R blocking antibodies, such as cixutumumab and ganitumab, show limited objective single-agent activity. Schoffski et al., Eur J Cancer., 49:3219-3228 (2013). Sorafenib, which inhibits Raf and several RTKs, has only minimal activity in patients with sarcomas. The mTOR inhibitor rapamycin and its derivatives, such as everolimus, cause cytostatic responses and are being evaluated in combination with other targeted drugs. However, a recent trial showed that combination of everolimus with bevacizumab, a monoclonal antibody that binds vascular endothelial growth factor (VEGF) and prevents activation of the RTK VEGF receptor, was not effective in patients with refractory MPNSTs. Widemann et al., J Clin Oncol., 34(15_suppl):11053-11053 (2016). A phase II study is ongoing to evaluate the dual mTOR complexes 1 and 2 inhibitor TAK-228 in soft-tissue sarcomas. Collectively, the modest and transient patient responses from the completed trials indicate that targeting more than one critical pathway is likely needed to achieve a cure.

To sustain uncontrolled growth, cancer cells commonly exhibit enhanced protein translation by upregulation of the translation machinery. The most highly regulated step in the protein biosynthetic pathway occurs during translation initiation, in which the eukaryotic initiation factor 4F (eIF4F) complex is recruited to the 5' untranslated region (UTR) of mRNA. This complex is composed of three subunits: eIF4G, a scaffolding protein; eIF4E, a cap-binding protein, and eIF4A, an RNA helicase which unwinds the secondary structure of the 5' UTR. The inventors have shown overexpression of the three eIF4F components in multiple types of human cancer, including MPNST. Oblinger et al., Exp Neurol., 299(Pt B):299-307 (2018). Genetic inhibition of eIF4A and eIF4E using shRNAs reduces MPNST cell proliferation. In addition, the pro-survival and pro-growth activities of several signaling pathways, such as the PI3K-AKT-mTOR and Raf-MEK-ERK frequently activated in human cancer, occur in part by facilitating eIF4F-mediated translation initiation. The mTOR kinase phosphorylates and inactivates the eIF4E-binding protein (4E-BP) translational repressors. Mamane et al., Oncogene, 25:6416-6422 (2006).

Both AKT and ERKs phosphorylate eIF4B, which then associates with and increases the helicase activity of eIF4A. Chu et al., Trends Cell Biol., 26:918-933 (2016), Moreover, AKT, mTOR, and the downstream ERK1/2 kinase p90 ribosomal S6 kinase can all phosphorylate and inactivate an endogenous repressor of eIF4A activity, the programmed cell death 4 (PDCD4) protein. Further, the mRNAs that depend upon eIF4A for efficient translation usually contain long 5' UTRs with guanine-rich sequences termed G-quadruplexes which can form four-stranded structures with G-tetrads stacked on one another. Malka-Mahieu et al., Clin Cancer Res., 23:21-25 (2017). These eIF4A-dependent transcripts are often found in genes encoding oncoproteins, transcription factors associated with super enhancers, epigenetic regulators, and kinases. Wolfe et al., Nature, 513: 65-70 (2014). Interestingly, the inventors also found that the eIF4A inhibitor silvestrol suppresses MPNST cell growth at low nanomolar of $IC_{50}$, decreases the levels of multiple mitogenic kinases including AKT and ERKs, and profoundly impairs the growth of MPNST xenografts. Oblinger et al., Neuro-Oncol., 18:1265-1277 (2016). These results suggest that direct targeting of the translation initiation components, particularly eIF4A, might be an effective treatment strategy for these tumors.

Silvestrol is part of a large family of compounds termed flavaglines or rocaglates, which share a cyclopenta[b]benzofuran structure. Kinghorn et al., Anticancer Res., 36:5623-

5637 (2016). It also possesses potent antitumor activity in multiple other cancer models. Boussemart et al., Nature, 513:105-109 (2014). However, silvestrol has some suboptimal drug-like properties. It is relatively large with a bulky dioxanyl ring, making the total synthesis of silvestrol laborious. Adams et al., J Am Chem Soc., 131:1607-1616 (2009). It is a substrate for the multidrug resistance 1 (MDR1) transporter (Gupta et al., AAPS J., 13:357-364 (2011)) and has very limited oral bioavailability of less than 2%. Saradhi et al., AAPS J., 13:347-56 (2011).

SUMMARY OF THE INVENTION

To search for compounds with better drug-like properties, ten rocaglates that lack the dioxanyl moiety were analyzed and the structure-activity relationships (SARs) for this compound class were examined. Pharmacokinetic analysis, an orthotopic MPNST cell line-derived xenograft and patient-derived xenograft (PDX) models for three types of sarcoma, and immunohistochemistry were employed to assess antitumor activity.

Didesmethylrocaglamide (DDR) and rocaglamide (Roc) possessed growth-inhibitory activity comparable to silvestrol. Both DDR and Roc arrested MPNST cells at G2/M, increased the sub-G1 population, induced cleavage of caspases and poly(ADP-ribose) polymerase, and elevated the levels of γH2A.X, while decreasing the expression of AKT and ERK1/2, consistent with translation inhibition. Unlike silvestrol, DDR and Roc were not sensitive to MDR1 efflux, Importantly, Roc had 50% oral bioavailability in mice and no pulmonary toxicity in dogs. When administered intraperitoneally or orally, it showed potent anti-tumor effects against MPNST xenografts. Treated tumors had more cleaved caspase 3-positive cells, indicative of increased apoptosis. Furthermore, Roc effectively suppressed the growth of Ewing sarcoma, osteosarcoma, and rhabdomyosarcoma cells and PDXs. Both Roc- and DDR-treated sarcoma cells showed decreased levels of multiple oncogenic kinases, including IGF-1R. The more favorable drug-like properties of Roc and DDR and the potent anti-tumor activity of Roc suggest that these rocaglamides could become viable treatments for MPNST and other sarcomas.

BRIEF DESCRIPTION OF THE FIGURES

The present invention may be more readily understood by reference to the following figures, wherein:

FIGS. 3A-3C provide graphs showing that, unlike silvestrol, DDR and Roe inhibits proliferation of MDR1-overexpressing 697-R leukemic cells at $IC_{50}$ values similar to parental silvestrol-sensitive 697 cells. Cell proliferation was measured on 697-R and parental 697 pre-B leukemia cells treated for 3 days with various concentrations of silvestrol (A), DDR (B), and Roc (C). Each treatment was performed in six replicates, and each experiment was repeated twice. Shown are representative dose-response growth inhibition curves from experiments for all three drugs that were run in parallel. The $IC_{50}$ values for individual growth curves are shown in the graph insets.

FIGS. 4A-4C provide graphs and images showing rocaglamide has 50% oral bioavailability and potently suppresses the growth of orthotopic ST8814-Luc MPNST xenografts. (A) Plasma concentration-time profiles of Roc. PK analysis was conducted as described in Methods. The mean concentration of Roc with standard deviation (SD) in mouse plasma after IV, IP, and PO administration was plotted for each indicated time point. For each dosing route, two independent studies were performed. (B) Shown are representative BL images of ST8814-Luc MPNST-bearing mice prior to (PreTx) and 4 weeks (wks) after treatment with Roc at 4 mg/kg by IP or 1.2 mg/kg by oral gavage (PO) or HPβCD vehicle every other day. (C) The relative tumor-emitted BL signals were denoted as % of total flux after treatment relative to the total flux prior to treatment designated as one (100%). The data are shown as mean±SD. For each treatment group, at least 7 mice completed the full treatment schedule. Note that tumor bioluminescence from vehicle-treated mice rapidly increased by an average of ~17,000-fold over four weeks; however, tumor bioluminescence from the Roc IP group only grew by an average of ~3-fold. Similarly, tumor bioluminescence from the Roc PO group grew only ~470-fold on average.

DETAILED DESCRIPTION OF THE INVENTION

Figure 1:
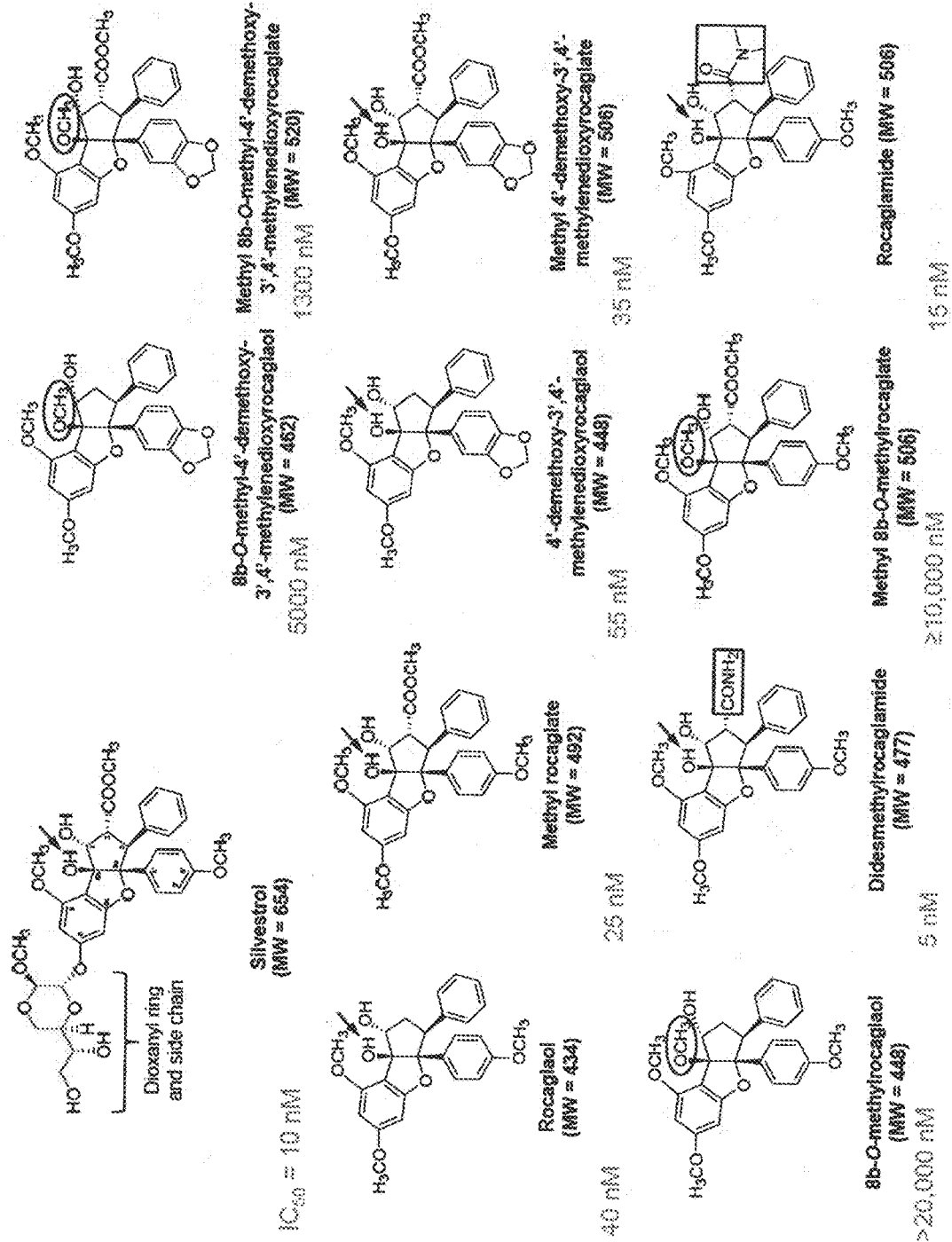
FIG. 1 provides chemical formulae showing identification of didesmethylrocaglamide and rocaglamide as having potent growth-inhibitory activity comparable to silvestrol. The structure of each rocaglate is shown along with its $IC_{50}$ value in STS26T MPNST cells as determined as shown in Table 1. Analysis of the structure-activity relationship revealed that the dioxanyl (dioxanyloxy) ring is dispensable but may enhance the cytotoxicity of rocaglates. An unmethylated C-8b hydroxyl group (indicated by an arrow) and the amide functionality (rectangle) of didesmethylrocaglamide and rocaglamide are important for optimum antiproliferative activity, while methylation of the C-8b hydroxyl group (oval) substantially impaired the activity.

The present invention provides a method of treating a nervous system cancer or soft-tissue sarcoma in a subject. The method includes administering a therapeutically effective amount of a compound according to formula I to a subject in need thereof:

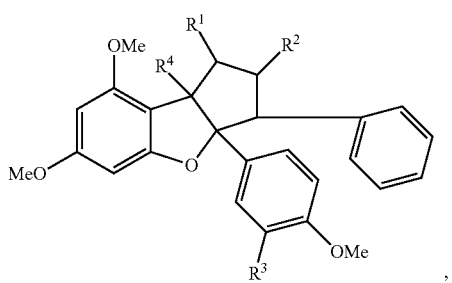

I wherein $R^1$ is selected from the group consisting of —OH, —OAc, —OCHO, =O, and =NOH; $R^2$ is selected from the group consisting of —CON(CH$_3$)$_2$, —CONHCH$_3$, —CONH$_2$, —COOCH$_3$, —COOH, and —H, $R^3$ is selected from the group consisting of —H, —OH, and —OCH$_3$, or $R^3$ is linked to the adjacent —OMe group to form a —O—CH$_2$—O— linkage, thereby forming a 3,4-benzodioxole, and $R^4$ is selected from the group consisting of —OH, —OCH$_3$, —OCH$_2$CH$_3$.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). In the context of the present invention, suitable organic groups for the compounds of this invention are those that do not interfere with the anti-cancer activity of the compounds. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alkyl groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

In some embodiments, two adjacent substituents of a benzyl ring are linked to form a —O—CH$_2$—O— linkage, thereby forming a 3,4-benzodioxole group, shown below in Formula II.

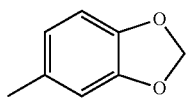

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated). In some embodiments, the compounds described herein are (−)-rocaglamide derivatives.

A subject, as defined herein, is an animal such as a vertebrate or invertebrate organism. In other embodiments, the subject is a mammal such as a domesticated farm animal (e.g., cow, horse, pig) or pet (e.g., dog, cat). More preferably, the subject is a human. A subject at risk is a subject who has been determined to have an above-average risk that a subject will develop cancer, which can be determined, for example, through family history or the detection of genes causing a predisposition to developing cancer. A subject who is a child is a non-adult subject. For example, a human subject under 18 years old is a child subject.

Treat", "treating", and "treatment", etc., as used herein, refer to any action providing a benefit to a subject at risk for or afflicted with a condition or disease such as cancer, including improvement in the condition through lessening or suppression of at least one symptom, delay in progression of the disease, prevention or delay in the onset of the disease, etc. The subject may be at risk due to exposure to carcinogenic agents, being genetically predisposed to disorders characterized by unwanted, rapid cell proliferation, and so on.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

Methods of Treating Nervous System Cancer or a Soft-Tissue Sarcoma.

In one aspect, the present invention provides a method of treating cancer in a subject in need thereof, comprising administering a therapeutically effective amount of a compound according to formula I to the subject:

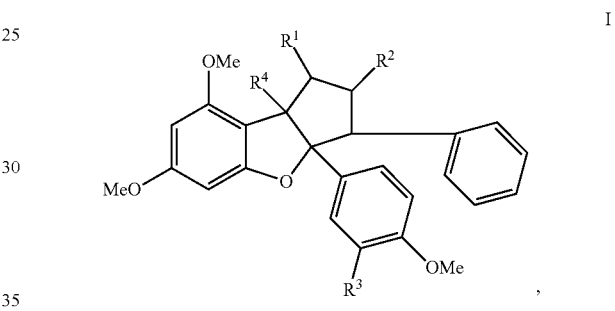

wherein R$^1$ is selected from the group consisting of —OH, —OAc, —OCHO, =O, and =NOH; R$^2$ is selected from the group consisting of —CON(CH$_3$)$_2$, —CONHCH$_3$, —CONH$_2$, —COOCH$_3$, —COOH, and —H, R$^3$ is selected from the group consisting of —H, —OH, and —OCH$_3$, or R$^3$ is linked to the adjacent —OMe group to form a —O—CH$_2$—O— linkage, thereby forming a 3,4-benzodioxole, and R$^4$ is selected from the group consisting of —OH, —OCH$_3$, —OCH$_2$CH$_3$, and wherein the cancer is a nervous system cancer or a soft-tissue sarcoma. The compounds according to formula I can also be referred to herein as rocaglamide derivatives.

One or more of the substituents of the compounds of formula I can be varied to provide additional embodiments of the invention. The compounds can be varied at different regions of the compounds. For example, R$^1$ can selected from the group consisting of —OH, —OAc, —OCHO, and =NOH, with —OH being a preferred moiety. The substituent R$^2$ can be selected from the group consisting of —CON(CH$_3$)$_2$, —CONHCH$_3$, —COOCH$_3$, —COOH, and —H, with amine containing moieties such as —CON(CH$_3$)$_2$, —CONHCH$_3$, and —CONH$_2$ being preferred. The substituent R$^3$ can selected from the group consisting of —H, —OH, and —OCH$_3$, with a hydrogen moiety being preferred. In some embodiments, R$^3$ is linked to the adjacent —OMe group to form a —O—CH$_2$—O— linkage, thereby forming a 3,4-benzodioxole. The substituent R$^4$ can selected from the group consisting of —OH, —OCH$_3$, and —OCH$_2$CH$_3$, with the moiety —OH being preferred. In some embodiments, the compound of formula I can be rocaglamide or didesmetyl-rocaglamide.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Cancer which has metastasized will still retain traits associated with its tissue of origin.

The anti-cancer compounds of the present invention are preferably used to treat nervous system cancer and soft-tissue sarcoma. A nervous system cancer is a type of cancer affecting the nervous system. Examples of nervous system cancer include nerve sheath tumor, brain tumor, arachnoid cyst, and optic nerve glioma. In some embodiments, the nerve sheath tumor is a malignant peripheral nerve sheath tumor. Nerve sheath tumors are found primarily in the myelin surrounding nerves, whereas a peripheral nerve sheath tumor is a nerve sheath tumor in the peripheral nervous system. Benign peripheral nerve sheath tumors include schwannomas and neurofibromas. A malignant peripheral nerve sheath tumor (MPNST) is a cancerous peripheral nerve sheath tumor.

In some embodiments, the cancer is a soft-tissue sarcoma. A soft-tissue sarcoma is a form of sarcoma that develops in connective tissue. Examples of soft-tissue sarcoma include fibrosarcoma, malignant fibrous histiocytoma, dermatofibrosarcoma, liposarcoma, rhabdomyosarcoma, leiomyosarcoma, hemangiosarcoma, Kaposi's sarcoma, lymphangiosarcoma, malignant peripheral nerve sheath tumor, chondrosarcoma, and osteosarcoma.

The rocaglamide derivatives can also be administered prophylactically to a subject prior to the development of cancer. Prophylactic administration, also referred to as prevention, is effective to decrease the likelihood that cancer will develop in the subject. For prophylactic treatment, the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on. In some embodiments, the subject has an increased risk of developing nervous system cancer or soft-tissue sarcoma.

The effectiveness of cancer treatment may be measured by evaluating a reduction in tumor load. The reduction in tumor load may be represent a direct decrease in mass, or it may be measured in terms of tumor growth delay, which is calculated by subtracting the average time for control tumors to grow over to a certain volume from the time required for treated tumors to grow to the same volume. Because MPNSTs overexpress eIF4F components, whose inhibition is correlated with inhibition of cell proliferation, eIF4A expression can also be used to evaluate the effectiveness of cancer treatment.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Methods of cancer treatment using the compounds described herein can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

Formulation and Administration of Anticancer Compounds

The present invention provides a method for administering one or more anti-cancer compounds in a pharmaceutical composition. Examples of pharmaceutical compositions include those for oral, intravenous, intramuscular, subcutaneous, or intraperitoneal administration, or any other route known to those skilled in the art, and generally involves providing an anti-cancer compound formulated together with a pharmaceutically acceptable carrier.

When preparing the compounds described herein for oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

For example, the maximum tolerated dose (MTD) for anticancer compounds can be determined in tumor-free athymic nude mice. Agents are prepared as suspensions in sterile water containing 0.5% methylcellulose (w/v) and 0.1% Tween 80 (v/v) and administered to mice (7 animals/group) by oral gavage at doses of 0, 25, 50, 100 and 200 mg/kg once daily for 14 days. Body weights, measured twice weekly, and direct daily observations of general health and behavior will serve as primary indicators of drug tolerance. MTD is defined as the highest dose that causes no more than 10% weight loss over the 14-day treatment period.

The anti-cancer compounds can also be provided as pharmaceutically acceptable salts. The phrase "pharmaceutically acceptable salts" connotes salts commonly used to for alkali metal salts and to form addition salts of free acids or free bases. The nature of the salt is not critical, provided that it is pharmaceutically acceptable. Suitable pharmaceutically acceptable acid addition salts of the compounds may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, γ-hydroxybutyric, galactaric, and galacturonic acids. Suitable pharmaceutically acceptable base addition salts of the compounds described herein include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds described herein. All of these salts may be prepared by conventional means from the corresponding compounds described herein by reacting, for example, the appropriate acid or base with the compound.

Preparation of Anticancer Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wisconsin, USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.) and similar texts known to those skilled in the art. Alternately, the compounds can be isolated from natural sources. For example, rocaglamide derivatives can be isolated from the tropical plant *Aglaia perviridis*. See Pan et al., Nat Prod Rep., 31:924-931 (2014), which also describes methods for the chemical synthesis of rocaglamide derivatives.

The present invention is illustrated by the following example. It is to be understood that the particular examples, materials, amounts, and procedures are to be interpreted broadly in accordance with the scope and spirit of the invention as set forth herein.

EXAMPLE

Targeting Protein Translation by Rocaglamide and Didesmethylrocaglamide to Treat MPNST and Other Sarcomas Methods Natural Compounds and Cells Ten silvestrol-related rocaglates, inclusive of (−)-didesmethylrocaglamide, were isolated from the tropical plant *Aglaia perviridis*, collected in Vietnam as part of a multi-institutional collaborative project on the discovery of new antineoplastic natural compounds. The full structures and absolute configurations of these rocaglates were determined. Pan et al., J Nat Prod., 76:394-404 (2013). For in vitro studies, purified silvestrol and related rocaglates were dissolved as a 10 mM stock in dimethyl sulfoxide (DMSO; Sigma-Aldrich). A 60-mg sample of (−)-rocaglamide (NSC326408) was prepared at the U.S. National Cancer Institute for in vivo studies.

The human MPNST cell lines, ST8814, STS26T, S462, T265, and luciferase-expressing ST8814-Luc, the human NF2-deficient meningioma cell line Ben-Men-1, the NJ2 mouse schwannoma cell line Sch10545, and primary human Schwann cells were propagated as previously described. Oblinger et al., Neuro-Oncol., 18:1265-1277 (2016). The Ewing sarcoma cell line A673 and the osteosarcoma cell lines, 143B and MG-63, were grown in Dulbecco's Modified Eagle's (DME) medium (Millipore-Sigma) supplemented with 10% fetal bovine serum (FBS; Atlanta Biological). The silvestrol-sensitive 697 and silvestrol-resistant 697-R pre-B acute lymphoblastic leukemia cells (Gupta et al., AAPS J., 13:357-364 (2011)), the Ewing sarcoma cell line TC32, the osteosarcoma cell lines, Saos2 and OS17, and the rhabdomyosarcoma cell line RD were cultivated in RPMI 1640 medium (Millipore-Sigma) plus 10% FBS.

Cell Proliferation Assays and Flow Cytometry

Actively-growing cells were seeded in 96-well plates (Sarstedt) at 2,000 cells/well for Ben-Men-1 and RD cells, 30,000 cells/well for 697 and 697-R cells, and 4,000 cells/well for all other cell lines. The following day, cells were treated with various concentrations of each compound or and 0.05% of DMSO as the control for six days for MG-63 cells or three days for all remaining cell lines. Cell proliferation was assessed using resazurin assays and the $IC_{50}$ value calculated. Cell cycle analysis was performed accordingly. Burns et al., Cancer Res., 73:792-803 (2013).

Western Blots

Subconfluent cells were treated with the indicated doses of Roc or DDR for 24-72 hours and then harvested in cell lysis buffer (Cell Signaling Technology) containing 1 mM phenylmethylsufonylfluoride and protease inhibitor cocktail (Sigma-Aldrich). The protein content in cleared lysates was quantitated using the microBCA assay (ThermoFisher). Equal amounts of protein were run in sodium dodecyl sulfate-polyacrylamide gels and electrotransferred onto Immobilon-FL PVDF membranes (Millipore). The antibodies used were directed against: MDR1/ABCB1 (#13978), insulin-like growth factor-1 receptor β subunit (IGF-1Rβ; #9750), AKT (#9272), ERK1/2 (#4695), glyceraldehyde-3-phosphate dehydrogenase (GAPDH; #5174), caspase-3 (#9662), caspase-7 (#9492), cleaved caspase-7 (#9491), poly(ADP-ribose) polymerase (PARP; #9532), cleaved PARP (#5625), and phospho-histone H2A.X (pH2A.X [$Ser^{39}$]; #9718; all from Cell Signaling Technology), NKX2.2 (sc-514161), LSD1 (sc-136174), and survivin (sc-17779; Santa Cruz Biotechnology), and FLI1 (ab15289) and cleaved caspase-3 (CC3; ab32042; Abcam). Protein bands were detected using IRDye® infrared fluorescent dye-labeled secondary antibodies and scanning on an Odyssey CLx imaging system (LI-COR Biosciences) using the appropriate fluorescent channel at a resolution of 84 μm.

Pharmacokinetic (PK) Analysis

Mice were administered with a 5 mg/kg dose of Roc by intravenous (IV) or intraperitoneal injection (IP) or by oral gavage (PO). Blood samples were collected before and at multiple indicated time-points after dosing (n=3). Plasma samples were obtained by centrifugation and stored at −80° C. To measure plasma concentrations of Roc, a sensitive liquid chromatography coupled with tandem mass spectrometry detection (LC/MS-MS) method was developed. The reference compounds Roc (NSC326408) and pipernyl rocaglate (NSC784086) were provided by the NCI Developmental Therapeutics Program with pipernyl rocaglate used as the internal standard for quantitation. Plasma samples were processed by taking 100 μl of plasma and adding 300 μl of methanol containing 0.05 μM of internal standard. The samples were vortexed and centrifuged at 10,000×g for 10 min. The supernatant was collected and evaporated to dryness. Dried samples were reconstituted in 100 μl of 1:1 water:acetonitrile and centrifuges at 10,000×g for 3 min, followed by injecting 10 μl into an HPLC. Compounds of interest were separated on a Kinetex EVO C18 column (150×2.1 mm) with a flow rate of 0.25 ml/min. Mobile phase consisted of 80% ammonium formate buffer (1 g/L) and 20% acetonitrile at the start of the run, and a linear gradient to 10% ammonium formate/90% acetonitrile was applied over 14 min. Roc and the internal standard were identified by MS/MS using a Thema) Vantage TSQ run in positive ion mode. The transitions used were m/z 506 to m/z 352 (Roc) and m/z 570 to m/z 450 (internal standard). Standard curves constructed in blank mouse plasma were found to be linear over the range of 0.001 μM (LOQ) to 2.5 μM of Roc. Samples found to be above 2.5 μM of Roc were reanalyzed after dilution with blank plasma. Absolute recoveries of Roc from plasma were to be >98%. AUC estimations were made manually using the trapezoidal method of integration.

Orthotopic Cell Line-Derived Xenograft (CDX) and Patient-Derived Xenograft (PDX) Models and In Vivo Efficacy All animal work was performed according to the protocols approved by the Institutional Animal Care and Use Committee at Nationwide Children's Hospital. For animal dosing, Roc was formulated in 30% hydroxypropyl-β-cyclodextrin (HPβCD; CTD, Inc.). To generate the orthotopic MPNST CDX model, ST8814-Luc cells were injected into the sciatic nerves of NSG mice (NOD.Cg-Prkdc$^{scid}$ Il2rg$^{tm1Wjl}$/SzJ; The Jackson Laboratory), followed by bioluminescence imaging (BLI) to monitor tumor growth. Burns and Chang, Methods Mol Biol., 1427:59-72 (2016). Mice bearing established ST8814-Luc tumors, as defined by increasing bioluminescence signals over at least two time points, were randomized into three groups (n=10 mice) and treated with the predetermined maximum tolerated dose (MTD) of Roc at 4 mg/kg by IP or 1.2 mg/kg by oral gavage, or the vehicle HPβCD every other day. Tumor growth was measured weekly by BLI. Following 4 weeks of treatment, tumors were harvested for histological analysis.

To generate PDX models, the Nationwide Children's Hospital Institutional Review Board approved the Human Subjects Protocol for the acquisition of surgically-removed tumor specimens from patients and informed patient consents were obtained. Shortly after resection, fresh tumor tissues with their histological types confirmed by a specialized pathologist were placed in Dulbecco's-modified Eagle (DME) medium (Invitrogen) and brought to the research laboratory. A piece of tumor fragment was implanted subcutaneously on the dorsal right flank area in an eight-to-ten week-old immunodeficient mouse under anesthesia. Tumors were allowed to grow until established, at which time the established PDX tumors were repeatedly passed from one animal to the next or cryopreserved. For Roc treatment, actively-growing PDXs for a Ewing sarcoma (NCH-EWS-2), an osteosarcoma (NCH—OS-7), and an alveolar rhabdomyosarcoma (NCH-ARMS-2) were excised and cut into 5-mm pieces. Each tumor piece was re-implanted into an NSG mouse and tumor growth was monitored. Once noted, the tumor sizes in the axial plane at its greatest dimension (L) and the orthogonal short dimension (S) were measured twice weekly using a Fowler Ultra-Cal Electronic Caliper. Approximated tumor volumes were calculated using the formula $V=(L \times S^2)/2$. Mice with growing tumors reaching ~100-200 mm$^3$ were randomized into two treatment groups (10 mice/group) for each PDX model and treated with 3 mg/kg of Roc or HPβCD by IP every other day, followed by tumor measurement twice weekly.

Immunohistochemistry

Sections from Roc or vehicle-treated MPNST tumors were prepared and stained with hematoxylin and eosin (H&E) or immunostained for p-histone H3(Ser$^{10}$) (pH3; ab32107, Abcam) or CC3 (#9664, Cell Signaling) as previously described. Burns et al., Cancer Res., 73:792-803 (2013).

Results

DDR and Roc Possess Potent Growth-Inhibitory Activity Comparable to Silvestrol.

Figure 2A:
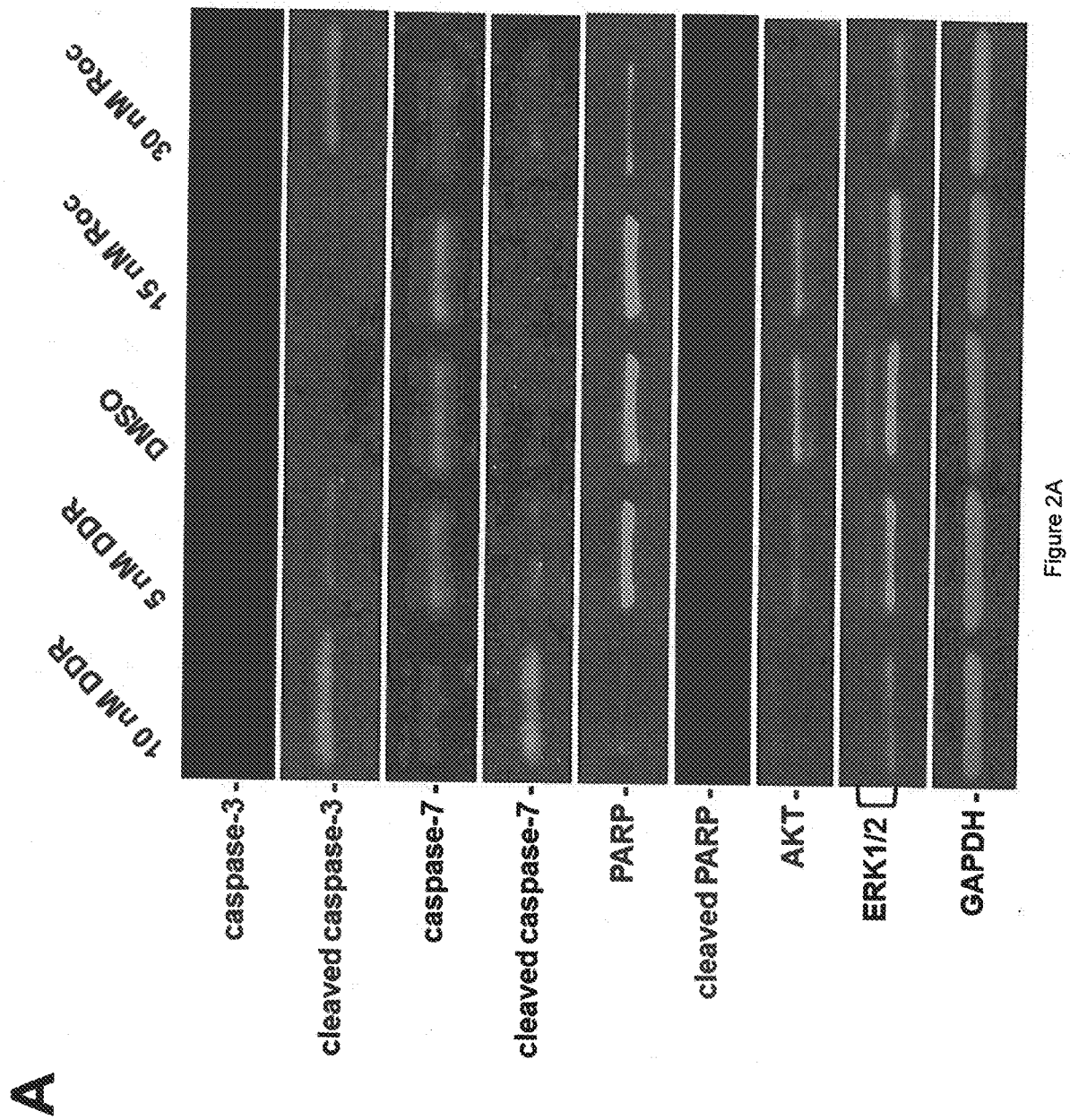
FIGS. 2A and 2B provide images showing that DDR and Roc increase caspase and PARP cleavage and elevated the levels of γH2AX while decreasing the expression of AKT and ERKs in MPNST cells. (A) Protein lysates prepared from STS26T cells treated for 3 days with 1 or 2 $IC_{50}$ of DDR or Roc were analyzed by Western blots for the expression of various apoptosis-related proteins and mitogenic kinases AKT and ERK1/2. GAPDH served as a loading control. (B) Western blot analysis was performed on lysates from STS26T cells treated for 1 and 2 days with 1 or 2 $IC_{50}$ of DDR for the expression of the DNA-damage response biomarker phosphorylated H2A.X (γH2A.X). As a positive control, lysates from HMS-97 human malignant schwannoma cells irradiated with 4 Grays (Gy) of X-ray were used.
Figure 2B:
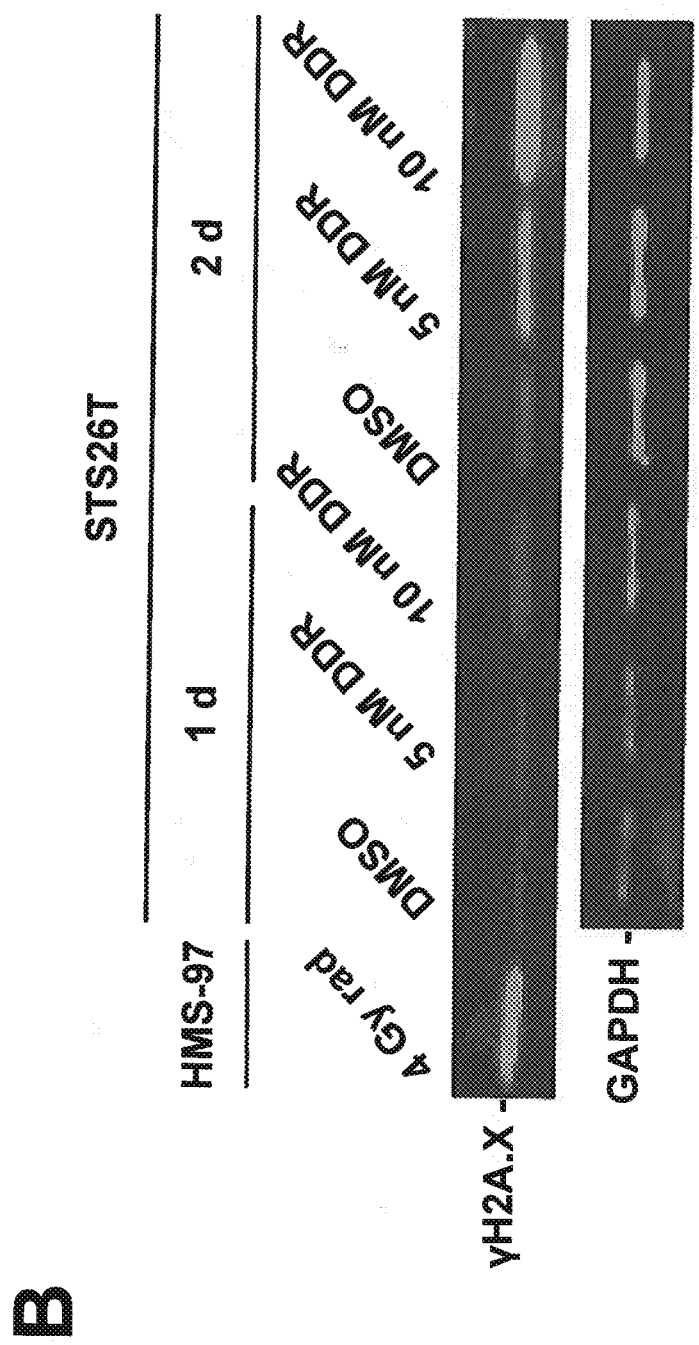

To search for compounds with better drug-like properties, the inventors conducted a side-by-side comparison of ten rocaglates lacking the dioxanyl ring with silvestrol for growth-inhibitory activity in a panel of MPNST, schwannoma, and meningioma cell lines, which they had previously shown to be sensitive to the antiproliferative action of silvestrol. The inventors found that several of these rocaglates maintained potent growth inhibition comparable to silvestrol. In particular, the $IC_{50}$ values of Roc were slightly higher than silvestrol, while DDR reliably demonstrated ~2-fold more potent than silvestrol in all cell lines tested (FIG. 1 and Table 1). The average $IC_{50}$ value of each rocaglate was determined by 3-day resazurin proliferation assays. These results show didesmethylrocaglamide (DDR) and rocaglamide (Roc) possess growth-inhibitory activity similar to or more potent than silvestrol, and indicate that the dioxanyl moiety is dispensable for cytotoxicity. Further structure and activity comparison discerned some positions on the cyclopenta[b]benzofuran scaffold that affected the antiproliferative activity of rocaglates. Similar to previous observations, the substitution of a methoxy group at position 8b, as seen with 8b-O-methylrocaglaol versus rocaglaol, abolished the activity (FIG. 1). This methoxy substitution at 8b could be partly mitigated by the addition of a methylenedioxy ring to phenyl ring B. Additionally, the presence of amide or ester groups at the C-2 position of the benzofuran scaffold appeared to enhance the activity, as compounds such as DDR, Roc, and methyl rocaglate were more potent than rocaglaol. Since the amide group at the C-2 position confers superior growth inhibition, DDR and Roc were further evaluated for their mechanisms of action.

several markers important for this process. STS26T cells treated for 3 days with either DDR or Roc exhibited increased cleavage of the initiator caspases 3 and 7 as well as their downstream substrate PARP (FIG. 2A). A concomitant decrease in the amounts of intact caspases 3 and 7 and PARP was observed, consistent with the enhanced cleavage of these apoptotic markers and possibly due to direct effects of these rocaglamides on protein translation. Likewise, the levels of the pro-survival kinases AKT and ERK1/2 were diminished in rocaglamide-treated MPNST cells. They also observed that treatment with rocaglamides resulted in higher levels of the DNA damage response marker γ-H2A.X. Importantly, this increase occurred as early as one day after DDR treatment before the occurrence of cell death (FIG. 2B). These results demonstrate that DDR and Roc induce apoptosis in MPNST cells, possibly subsequent to the activation of the DNA damage response.

Rocaglamides are not Sensitive to MDR1 Inhibition and Roc is Orally Bioavailable.

The MDR1/P-glycoprotein (Pgp) encoded by the ABCB1 (ATP-binding cassette subfamily B member 1) gene is implicated in limiting the bioavailability of several chemo-

TABLE 1

The growth-inhibitory activity of silvestrol and 10 related rocaglates lacking the dioxanyl ring

| | | IC50 (nM) | | | |
|---|---|---|---|---|---|
| Compound | MW (Da) | Sch10545 Nf2$^{-/-}$ schwannoma cells | Ben-Men-1 NF2$^{-/-}$ meningioma cells | STS26T NF1$^{+/+}$ MPNST cells | ST8814 NF1$^{-/-}$ MPNST cells |
| Silvestrol | 654 | 70 | 10 | 10 | 40 |
| 8b-O-methyl-4'-demethoxy-3',4'-methylenedioxyrocaglaol | 462 | >2,500 | >2,500 | 5,000 | 10,000 |
| Methyl 8b-O-methyl-4'-demethoxy-3',4'-methylenedioxyrocaglate | 520 | 1,900 | 3,800 | 1,300 | 2,000 |
| Rocaglaol | 434 | 60 | 100 | 40 | 90 |
| Methyl rocaglate | 492 | 50 | 55 | 25 | 35 |
| 4'-demethoxy-3',4'-methylenedioxyrocaglaol | 448 | 65 | 85 | 55 | 120 |
| Methyl 4'-demethoxy-3',4'-methylenedioxyrocaglate | 506 | 60 | 80 | 35 | 70 |
| 8b-O-methylrocaglaol | 448 | >20,000 | >20,000 | >20,000 | >20,000 |
| Didesmethylrocaglamide | 477 | 10 | 5 | 5 | 5 |
| Methyl 8b-O-methylrocaglate | 506 | 9,300 | >10,000 | ≥10,000 | >20,000 |

Rocaglamides Induce $G_2/M$ Arrest and Cell Death.

Flow cytometry analysis revealed that human NF1-expressing STS26T and NFL-null ST8814 MPNST cells treated with one- or two-$IC_{50}$ doses of DDR or Roc for three days exhibited a marked increase in the GVM fraction. The sub-$G_1$ fraction, suggestive of apoptosis, was noticeably prominent in treated STS26T cells, especially at the two-$IC_5O$ dose. Phase contrast micrographs taken of these cells prior to cell cycle analysis showed increased debris and floating dead cells in DDR or Roc-treated dishes. While ST8814 cells treated for three days did not show obvious signs of cell death, a six-day incubation resulted in increased numbers of floating dead cells with a commensurate expansion of the sub-$G_1$ fraction. Collectively, these results indicate that, like silvestrol, DDR and Roc inhibit MPNST cell proliferation by inducing cell cycle arrest at $G_2/M$ and subsequently, cell death.

DDR and Roc increase caspase and PARP cleavage and activate the DNA damage response, while suppressing mitogenic signaling pathways.

To confirm induction of apoptosis in rocaglamide-treated MPNST cells, the inventors analyzed protein expression of therapeutics and confers drug resistance in tumors that overexpress this protein. Previously, Gupta et al. showed that silvestrol is a substrate of MDR1/Pgp, which may be related to its poor oral bioavailability. Saradhi et al., AAPS J., 13:347-56 (2011). To determine whether there are any differences in the sensitivity to MDR1/Pgp between rocaglamides and silvestrol, the inventors treated silvestrol-resistant 697-R leukemic cells, which overexpress MDR1/Pgp, and the parental silvestrol-sensitive 697 cells with various concentrations of each compound. Similar to previous findings (Gupta et al., AAPS J., 13:357-364 (2011)), the inventors found that 697-R cells were less sensitive to silvestrol inhibition than 697 cells (26 nM vs 3.5 nM of $IC_{50}$, respectively; FIG. 3A). Surprisingly, DDR- and Roc-treated 697-R cells exhibited $IC_{50}$ values very similar to those of parental 697 cells (FIGS. 3B and 3C), indicating that these rocaglamides are no longer sensitive to MDR1 inhibition.

To examine the oral bioavailability, PK studies were conducted to compare mice that had been dosed with Roc at 5 mg/kg via the IV, IP, or PO route, followed by measuring Roc concentrations in blood samples collected at various times post dosing. Two separate studies with three mice at each time point for each route of dosing were conducted. The maximum mean observed concentration ($C_{max}$) reached ~11 µM for the IV route, ~4 µM for the IP route, and ~0.8 µM for the PO route (FIG. 4A). Areas under the plasma concentration-time curves ($AUC_{0-7h}$) produced 245 µM min of exposure in the IV route and 142 µM min of exposure in the PO route. The concentrations of Roc appeared to more slowly decline in the plasma over 24 h ($T_{1/2}$=2.4 hour) with the PO route compared to those dosed by IV route ($T_{1/2}$=~1.5 hour). Based on the estimation from $AUC_{0-7h}$, Roc exhibited ~50% oral bioavailability, confirming improved bioavailability of Roc over silvestrol.

Roc, when administered intraperitoneally or orally, exhibits potent anti-tumor effects in an orthotopic MPNST model.

To evaluate the in vivo activity of Roc, the inventors treated NSG mice bearing luciferase-expressing ST8814-Luc tumors implanted in the sciatic nerve with Roc at the predetermined MTD (4 mg/kg by IP or 1.2 mg/kg oral gavage), or IPβCD as the vehicle control every other day. As shown in FIGS. 4B and 4C, tumor bioluminescence from vehicle-treated mice steadily and rapidly increased by more than 10,000-fold over the four-week treatment period. In contrast, tumor bioluminescence from mice treated with Roc by IP only increased by an average of less than 10-fold, showing >99% reduction in tumor luminescence compared to controls (FIGS. 4C and 4D). Similarly, Roc, when administered orally, also exhibited potent tumor inhibition with bioluminescence decreasing by >95% (FIGS. 4C and 4E).

Figure 5:
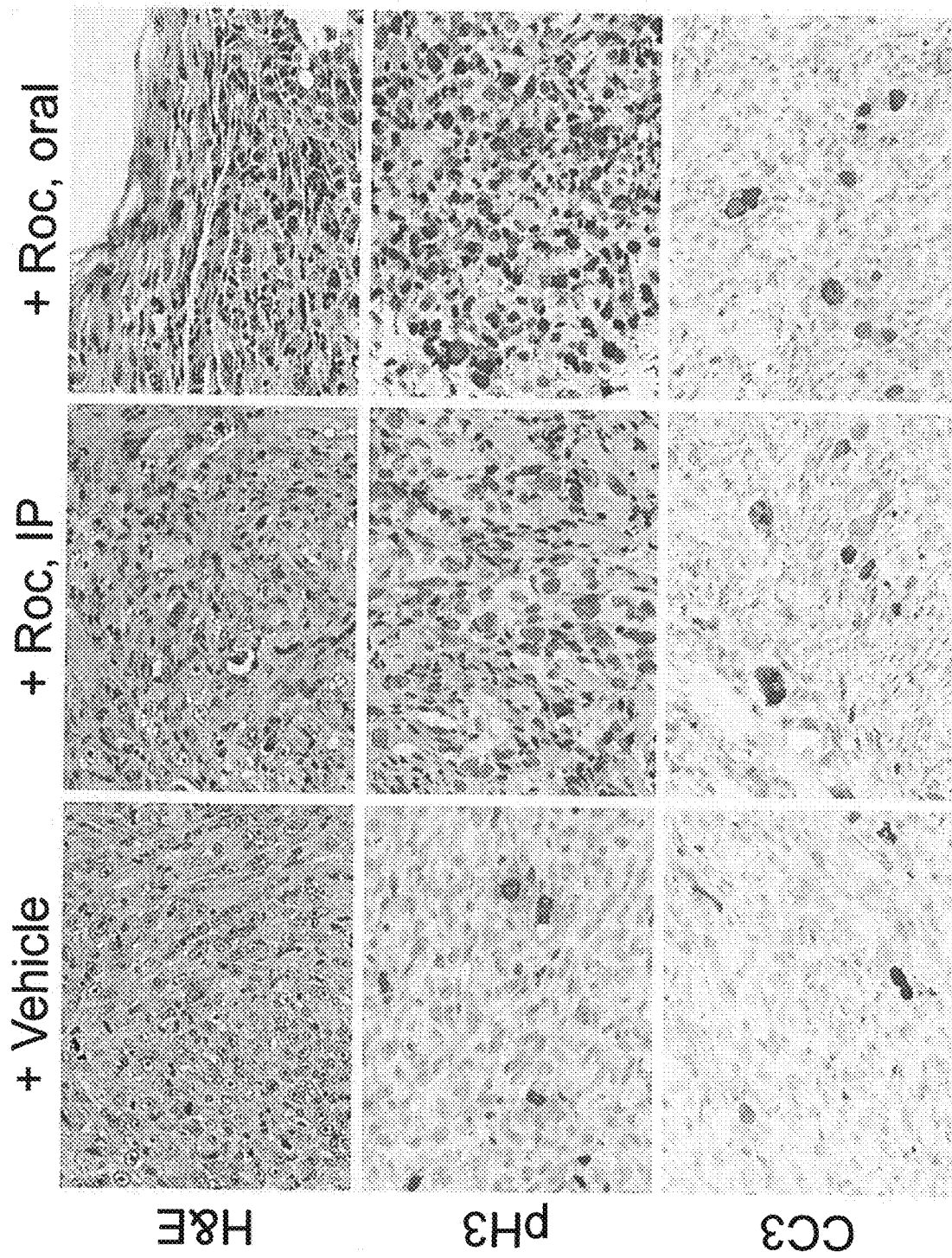
FIG. 5 provides images of MPNST xenografts treated with Roc by IP or oral gavage display degenerative changes and have more apoptotic cells. ST8814-Luc MPNST xenografts treated with HPβCD vehicle or Roc by IP or oral gavage for 4 weeks were processed for IHC analysis. (Top panels) H&E staining showed that vehicle-treated tumor cells had large vesicular nuclei with prominent nucleoli and displayed active mitotic activity. In contrast, tumor cells treated with Roc by IP had pleomorphic nuclei, and many enlarged tumor cells with abundant foamy cytoplasm resembling histiocytoid degenerative changes were noted along with scattered apoptosis. Degenerative tumor cells were also present in tumors treated with orally-delivered Roc. Tumor necrosis with necrotic debris separating mostly degenerative tumor cells with viable vasculature was also observed. (Middle panels) Immunostaining revealed abundant phospho-histone H3 (pH3)-labeled cells in Roc-treated tumors compared to vehicle-treated tumors. (Bottom panels) Increased numbers of cleaved caspase-3 (CC3)-positive cells were also detected in Roc-treated tumors.

Histological staining of tumor sections revealed that MPNSTs treated with HPβCD for four weeks had large nuclei with prominent nucleoli and displayed active mitotic figures (FIG. 5, top left panel). Conversely, tumors treated with Roc by IP had pleomorphic nuclei with abundant foamy cytoplasm resembling histiocytoid degenerative changes (top middle panel). A few enlarged tumor cells that appeared multinucleated and scattered apoptosis were present, Degenerative changes and cell death were also observed in tumor cells treated with orally-delivered Roc (top right panel). Consistent with $G_2$/M arrest, tumor cells treated with IP- or orally-delivered Roc exhibited much higher prevalence of phospho-histone H3 labeling compared to vehicle-treated tumors (middle panels). In addition, Roc-treated tumors displayed increased numbers of cleaved caspase-3 positive cells which often coincided with those with multinucleated-like appearance (bottom panels). Taken together, these results indicate that Roc has oral bioavailability and possesses potent in vivo efficacy against MPNSTs.

Roc and DDR have broad antitumor activity against common types of pediatric sarcoma.

Since MPNSTs comprise only ~2% of all sarcomas (Farid et al. Oncologist, 19:193-201 (2014)), the inventors expanded their testing of Roc and DDR to three other more prevalent sarcomas particularly in children and young adults: Ewing sarcoma, osteosarcoma, and rhabdomyosarcoma. Using a series of commonly used cell lines, including two Ewing sarcoma cell lines (A673 and TC32), four osteosarcoma cell lines (143B, MG-63, Saos2, and OS17), and one rhabdomyosarcoma cell line (RD), they found that, as in MPNST cells, both rocaglamides were highly active against all of these sarcoma cell lines. Also, they observed that DDR consistently exhibited lower $IC_5O$ values than Roc in every sarcoma cell line tested.

Figures 6A, 6B:
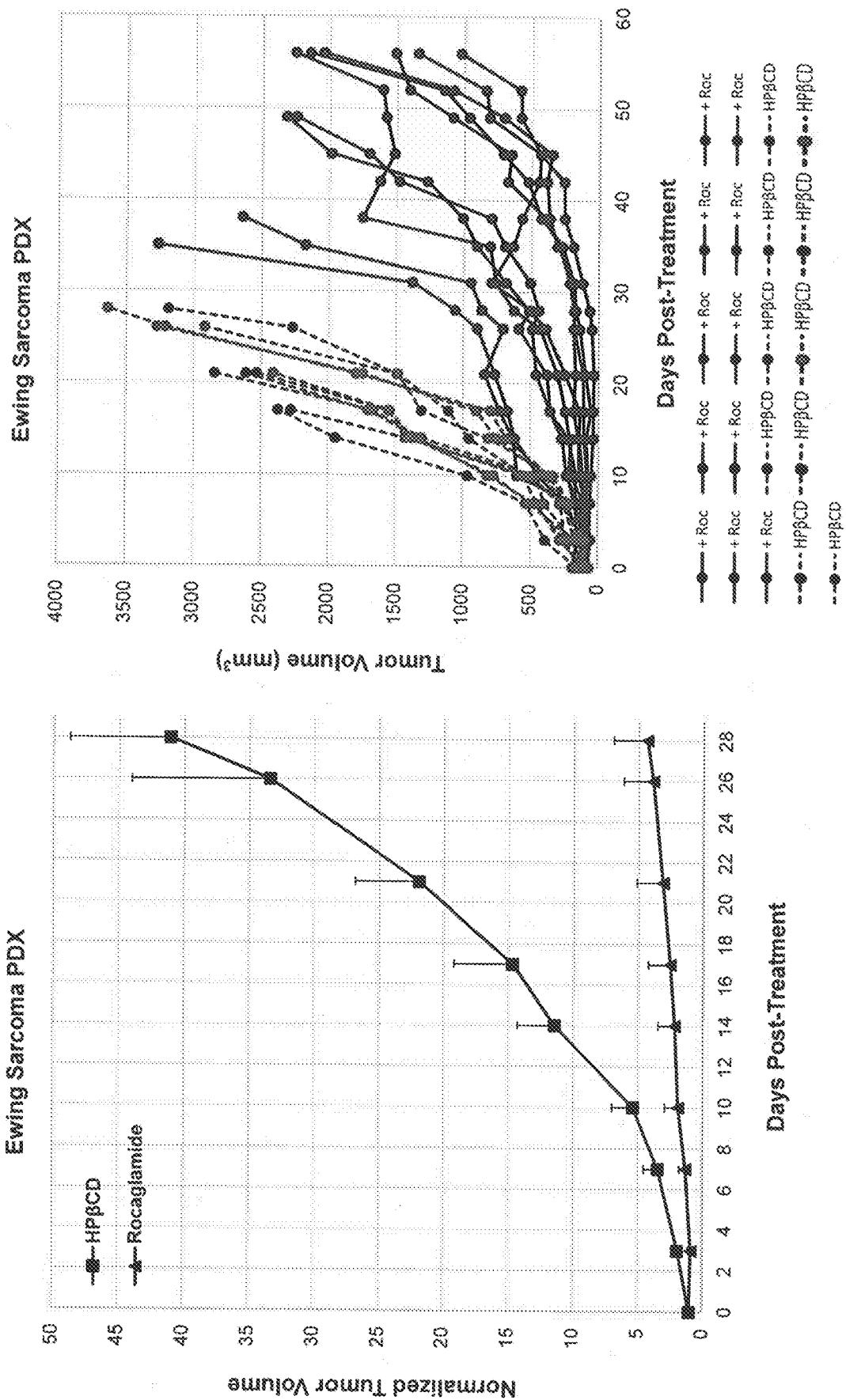
FIGS. 6A-6F provide graphs showing rocaglamide exhibits potent anti-tumor effects in multiple types of sarcoma. Mice with growing Ewing sarcoma (A-B), osteosarcoma (C-D), and rhabdomyosarcoma (E-F) PDX tumors were treated with 3 mg/kg of Roc or HPβCD vehicle delivered by IP every other day. Tumor diameters were measured twice weekly and volumes were calculated according to Methods. The normalized tumor volumes, denoted as the ratio of the calculated tumor volume after treatment relative to the volume prior to treatment designated as one, were plotted as the mean tumor volume of the entire treatment group at each time point with SD (A, C, and E). The calculated tumor volumes for each individual mouse over time were also plotted (B, D, and F).
Figure 6D:
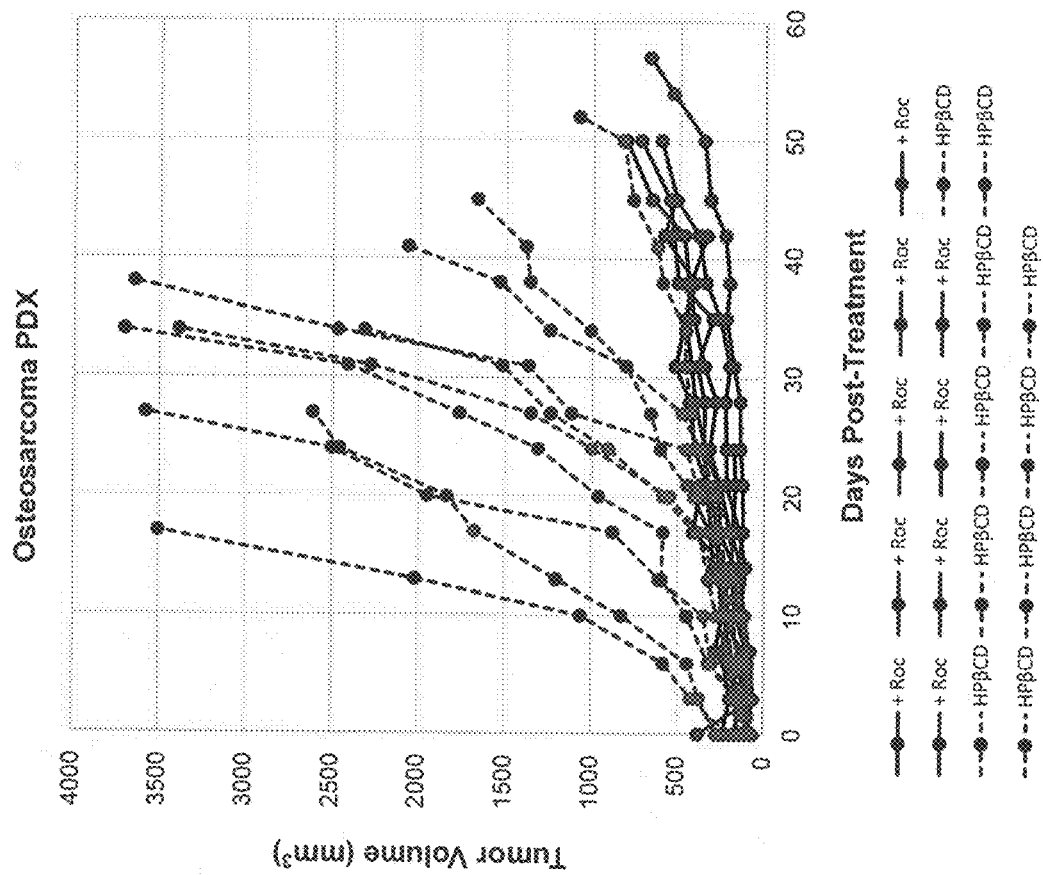
Figure 6C:
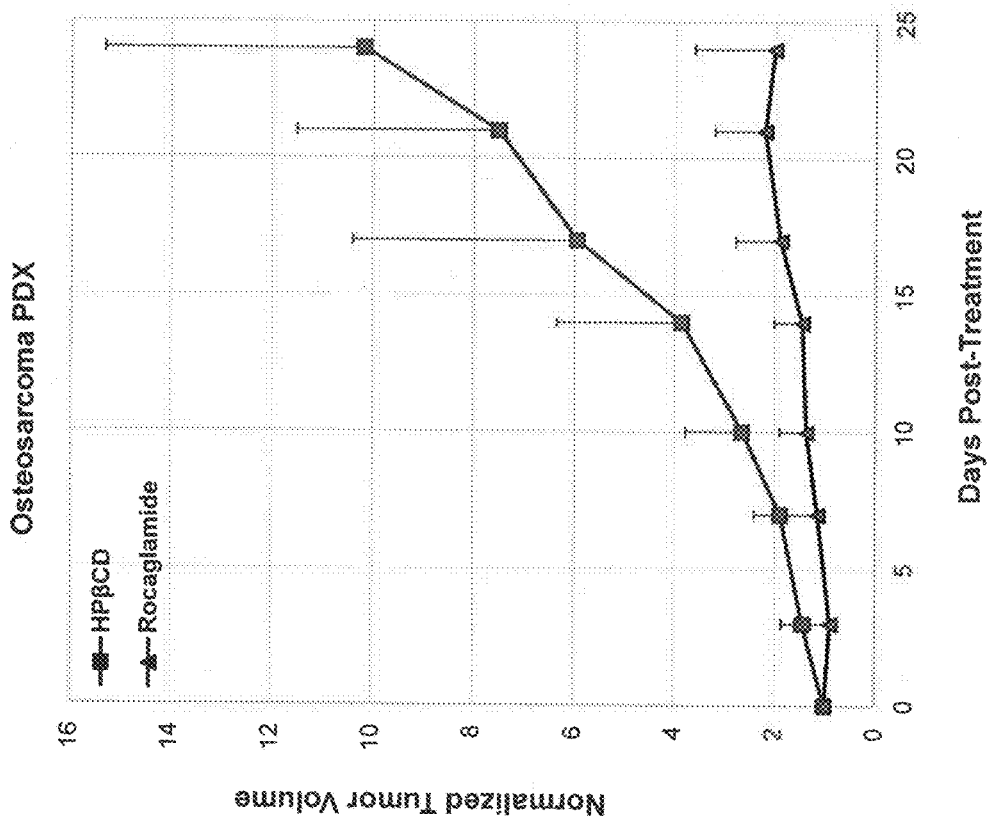
Figures 6E, 6F:
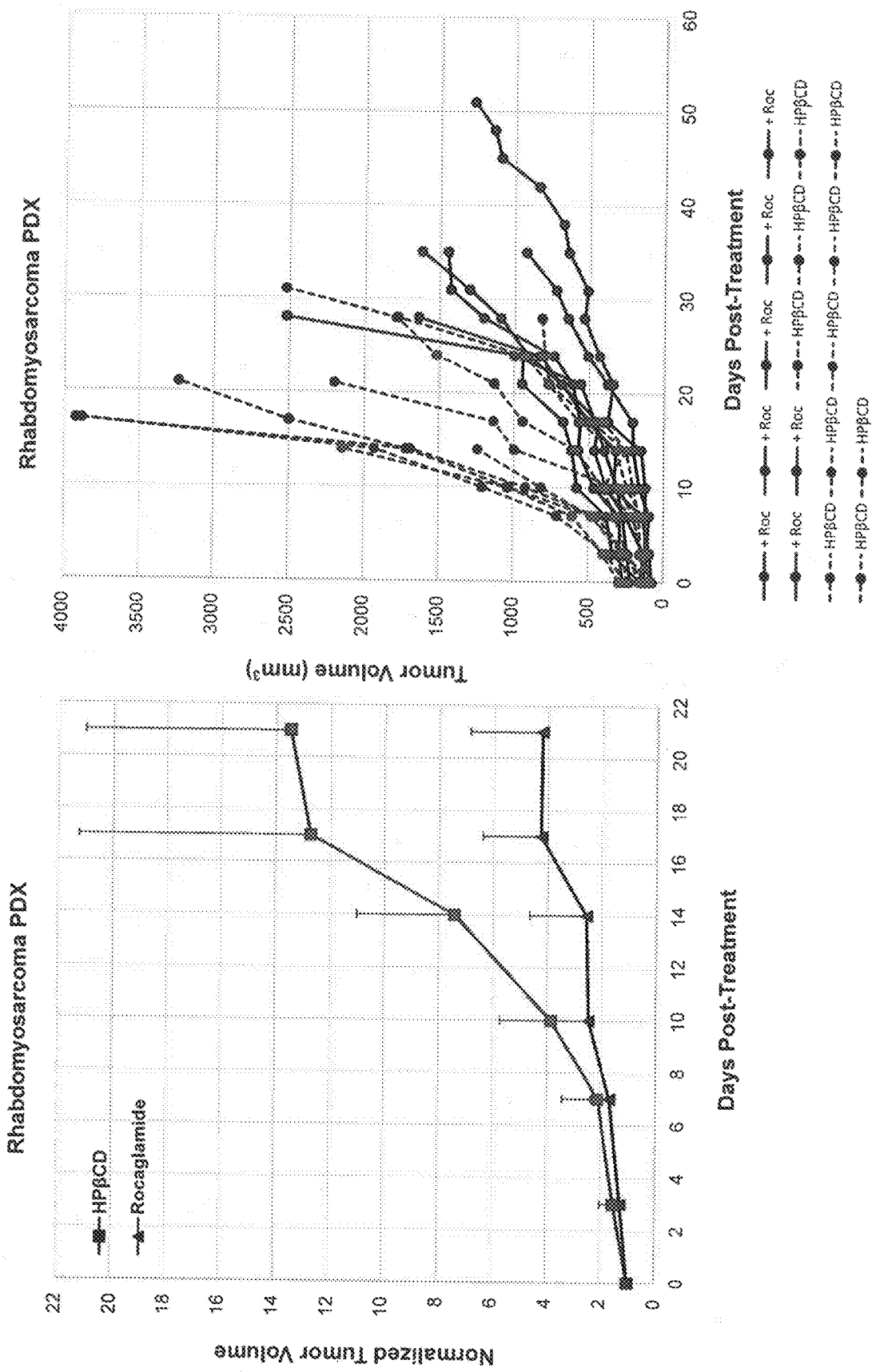

Subsequently, the inventors evaluated the in vivo activity of Roc in PDX models for a Ewing sarcoma, an osteosarcoma, and an alveolar rhabdomyosarcoma. They discovered that Roc was highly potent in suppressing the growth of Ewing sarcoma PDXs and inhibited tumor growth by an average of ~90% over four weeks of treatment (FIG. 6A). Similarly, the average size of Roc-treated osteosarcoma PDX tumors was reduced by ~80% compared to those of vehicle-treated tumors (FIG. 6B). Also, Roc reduced tumor growth in rhabdomyosarcoma PDXs by ~70% (FIG. 6C). Notably, the volumes of tumors in individual Roc-treated mice showed very little overlap with those in vehicle-treated mice, particularly for the Ewing sarcoma and osteosarcoma PDX models (FIG. 6). Together with the findings from the MPNST model, these results demonstrate that Roc displays significant antitumor effects against multiple types of sarcoma.

Rocaglamides decrease multiple signaling kinases and transcription factors important for sarcoma cell growth.

Figure 7A:
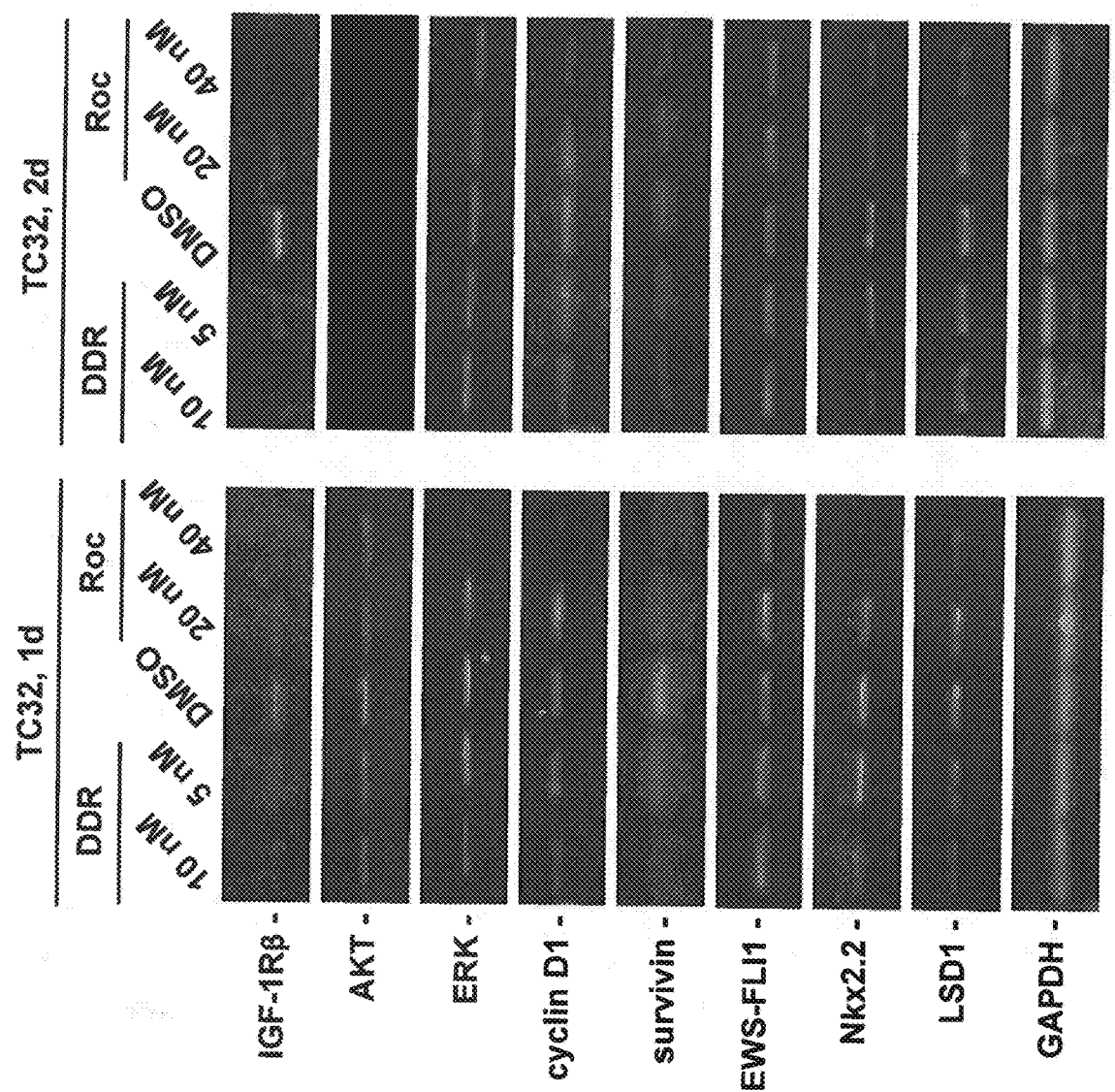
FIGS. 7A-7C provide images showing DDR and Roc reduce multiple signaling proteins important for the growth and survival of sarcoma cells. Lysates prepared from TC32 Ewing sarcoma (A), 143B osteosarcoma (B), and RD rhabdomyosarcoma (C) cells were treated 1 and 2 days with the indicated concentrations of DDR or Roc and analyzed by Western blotting for the expression of various oncogenic driver proteins. GAPDH was used as a loading control.
Figure 7B:
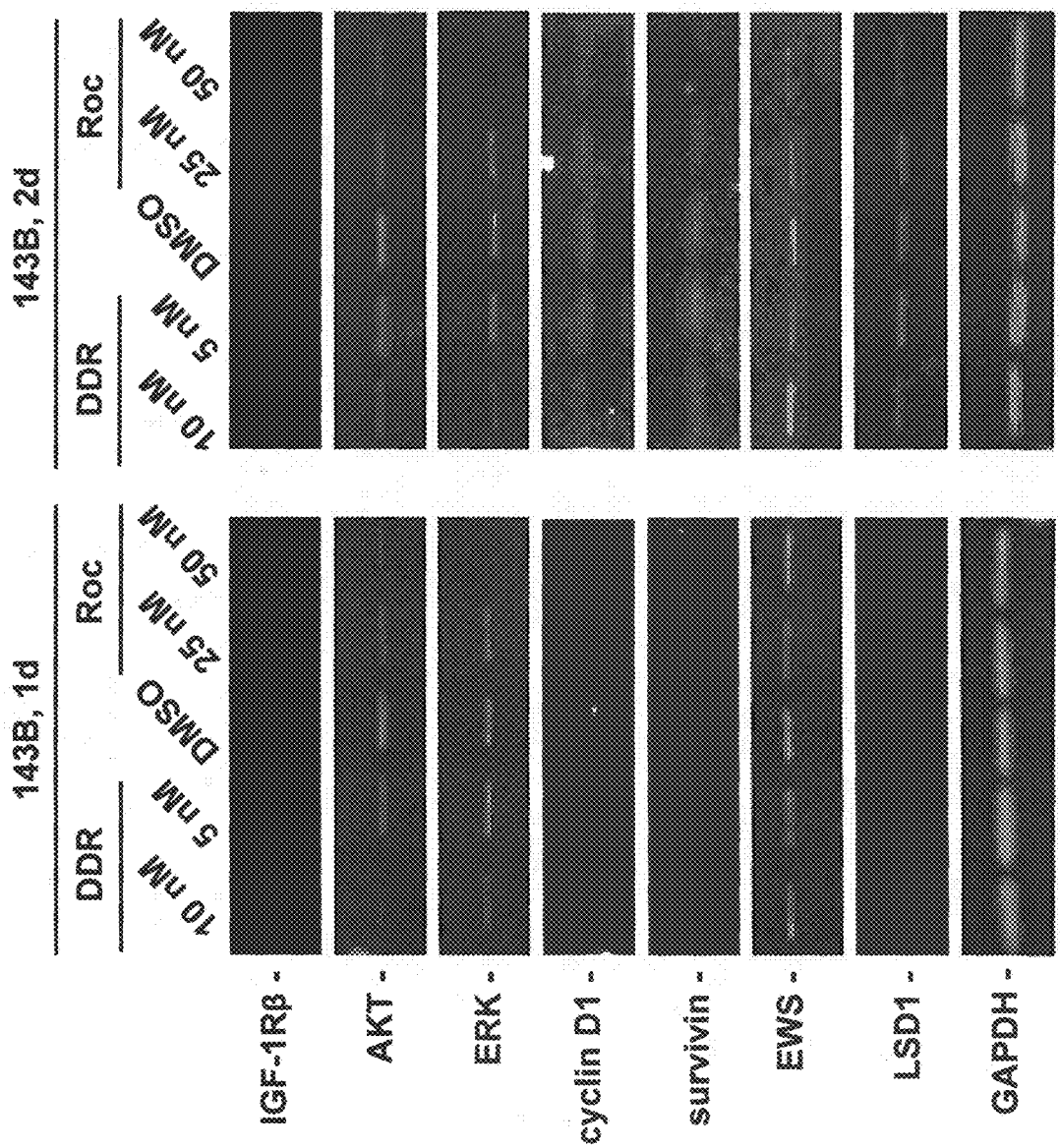
Figure 7C:
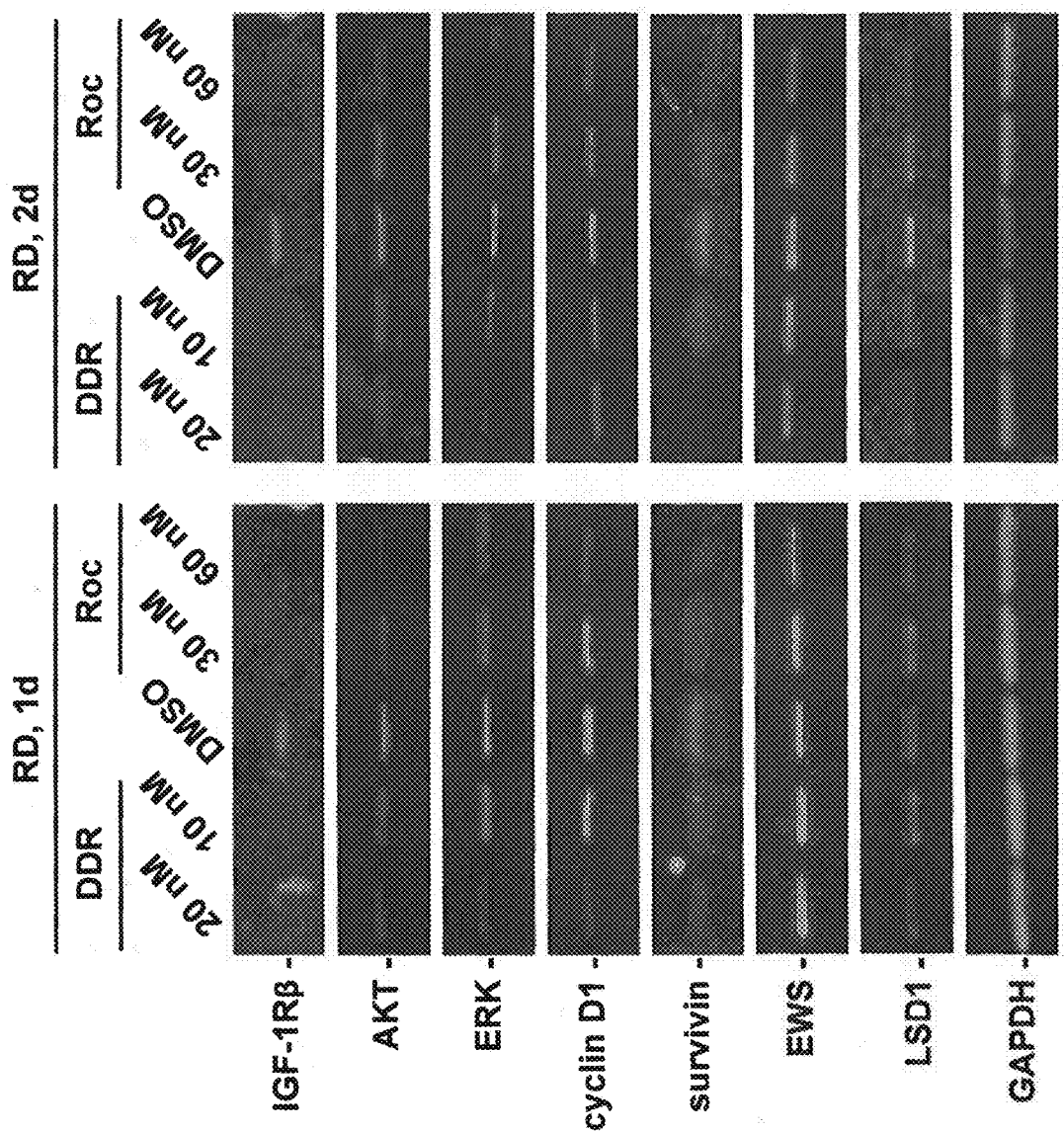

To further examine the molecular mechanisms underlying the antiproliferative effects of rocaglamides, the inventors treated TC32 Ewing sarcoma, 143B osteosarcoma, and RD rhabdomyosarcoma cells with 1- or 2-$IC_{50}$ dose of DDR or rocaglamide for 1-2 days followed by Western blotting for several known drivers of cell survival and proliferation. Interestingly, they found that these rocaglamides reliably reduced the levels of the β subunit of IGF-1R, an upstream activator of PI3K-AKT signaling, in all three sarcoma cell lines (FIGS. 7A-C). They also observed reduction of the IGF-1Rβ levels in rocaglamide-treated MPNST cells. In addition, Roc and DDR decreased the levels of AKT, ERKs, cyclin D1 and survivin in treated TC32, 143B, and RD cells (FIG. 7). Intriguingly, the oncogenic fusion protein EWS-FLI1, which acts as an aberrant transcription factor in Ewing sarcoma, was not affected in Roc- and DDR-treated TC32 Ewing sarcoma cells (FIG. 7A). Consistent with this observation, these rocaglamides did not inhibit EWS expression in 143B osteosarcoma and RD rhabdomyosarcoma cells (FIGS. 7B-C). However, the expression of lysine demethylase 1 (LSD1), which modulates EWS-FLI1 transcriptional activity (Sankar et al., Oncogene, 32:5089-5100 (2013)), and NKX2.2, an EWS-FL11-regulated gene necessary for oncogenic transformation (Smith et al., Cancer Cell, 9:405-416 (2006)), were diminished by these rocaglamides in TC32 cells (FIG. 7A). Collectively, these results suggest that rocaglamides potently suppress sarcoma growth by decreasing multiple key signaling proteins important for tumor growth and survival.

Discussion

For decades, treatments for MPNSTs and other sarcomas have remained largely unchanged with current standard of care combining surgical resection with intensive multi-agent chemotherapy. Skapek et al., Nat Rev Dis Primers, 5:1 (2019). Radiation may be used depending upon the tumor type and clinical presentation. While this multidisciplinary treatment strategy may help control local disease, it is not effective for metastatic and recurrent disease. Also, these multimodal regimens are associated with considerable acute and long-term toxicities that compromise health-related quality of life in survivors. Despite recent advances in understanding tumor biology and targeted therapy development, an FDA-approved medical therapy for the treatment of these malignancies is still not available. The inventors previously showed that eIF4A is a vulnerable point of disruption in MPNSTs and that the eIF4A inhibitor silvestrol potently suppresses MPNST growth. Regretfully, silvestrol exhibited an unexpected pulmonary toxicity in dogs and its further development as a cancer therapy was suspended. Kinghorn et al., Anticancer Res., 36:5623-5637 (2016). The inventors have identified two rocaglates lacking the dioxanyl ring, Roc and DDR, with better drug-like properties than silvestrol and possessing antitumor efficacy in multiple sarcoma models, including MPNST. Most critically, a recent toxicity study conducted by the NCI Developmental Therapeutics Program revealed that Roc did not induce the toxicity found in dogs with silvestrol under the same conditions.

A side-by-side comparison of 10 rocaglates lacking the bulky dioxanyl ring present in silvestrol has allowed the inventors to discern certain structure-activity relationships, particularly the C-8b, C-2, and C-6 positions along the cyclopenta[b]benzofuran core. Consistent with previous reports (Ebada et al., Prog Chem Org Nat Prod., 94:1-58 (2011); Kinghorn et al., Anticancer Res., 36:5623-5637 (2016)), the hydroxy group at the C-8b position is essential for antiproliferative activity. This finding is consistent with the crystal structure of Roc complexed to eIF4A and polypurine RNA, which reveals hydrogen bonding between the 8b-OH of Roc and a guanine base in the RNA. Iwasaki et al., Mol Cell., 73:738-748 (2019). Also, the phenyl rings A and B of Roc parallel stack with RNA bases, which may explain our finding that adding a methylenedioxy group to ring B modestly improved the growth inhibitory activity of rocaglates with methylated 8b-OH (FIG. 1). It is possible that this methylenedioxy ring may enhance the affinity of the rocaglates to the eIF4A-RNA complex, partially compensating for the loss of 8b hydrogen bonding.

Among the rocaglates lacking the dioxanyl ring that were evaluated, DDR was the most potent, suggestive of the importance of having a simple primary amide group at the C-2 position. While the presence of a dioxanyl ring instead of a methoxy group at the C-6 position enhances the potency of silvestrol compared with methyl rocaglate (Kim et al., Anticancer Agents Med Chem., 6:319-345 (2006), the inventors' data indicated that this ring is not required for cytotoxicity; however, it appears to play an important role in MDR1-induced resistance as Roc and DDR are no longer susceptible to this inhibitory effect. Consistent with this notion, they detected a higher level of MDR1 in ST8814 MPNST cells than that in STS26T cells, while the $IC_{50}$ values of Roc and DDR in ST8814 cells were similar to those in STS26T cells. The MDR1 transporter binds to silvestrol and is thought to limit its oral bioavailability. A PK analysis demonstrating 50% oral bioavailability of Roc, a >25-fold improvement over silvestrol, confirms this prediction and strongly suggests a possible interaction of MDR1 with the dioxanyl moiety. The oral bioavailability of Roc that we observed allows a greater flexibility for dosing. More importantly, they found that Roe, when administered intraperitoneally or orally, showed potent anti-tumor effects in an orthotopic MPNST CDX mouse model and effectively suppressed the growth of PDX models for Ewing sarcoma, osteosarcoma, and rhabdomyosarcoma.

Like silvestrol, rocaglamides exert their potent growth-inhibitory and antitumor activities mainly through inhibition of eIF4A and protein translation. Sadlish et al., ACS Chem Biol., 8:1519-1527 (2013). Consistently, the inventors observed that Roe and DDR decreased the levels of multiple signaling proteins important for tumor growth and survival, leading to $G_2$/M cell cycle arrest and activation of executioner caspases. In addition to AKT and ERKs, rocaglamides also reduced the expression of IGF-1R in all sarcoma cell lines tested. This decrease in IGF-1R, coupled with the simultaneous inhibition of AKT and ERKs, likely results in superior inhibition of IGF-1 signaling compared to the simple blockade at the receptor level. Simpson et al., Target Oncol., 12:571-597 (2017). The results further suggest that IGF-1R may serve as a biomarker for responsiveness to rocaglamides in sarcomas.

It should be noted that the effects of translation inhibition mediated by eIF4A are different from those by eIF4E, which can be activated by the AKT/mTOR pathway, a common deregulated event in sarcomas. Mamane et al., Oncogene, 25:6416-6422 (2006). Rapamycin and its analogs and mTOR kinase inhibitors, which block mTOR signaling, only exhibit cytostatic effects and tumor stabilization. D'Abronzo and Ghosh, Neoplasia, 20:563-573 (2018). Also, inhibition of mTOR signaling is associated with the activation of bypass signaling pathways that can restore critical survival signals and enabling tumor regrowth. The inhibition of eIF4E tends to decrease the translation of mRNAs with 5' terminal oligopyrimidine tracts, which encode ribosomal proteins, elongation factors, lysosomal-related and metabolic-related proteins. However, eIF4A activity is more critical in the unwinding mRNAs with long 5' UTRs that can form G-quadruplexes, such as AKT and IGF-1R. In addition, some transcripts, e.g., c-MYC, are translated from internal ribosomal entry sites that do not require the presence of eIF4E and are insensitive to eIF4E inhibition. Wiegering et al., Cancer Discov., 5:768-781 (2015). Thus, blocking eIF4A may have a stronger effect on tumor growth and survival.

Ewing sarcoma is frequently driven by the chimeric fusion oncogene EWS-FLI1 due to a chromosomal translocation that fuses an RNA-binding protein, EWSR1, with the FLI1 transcription factor. Surprisingly, the inventors found that the levels of EWS-FLI1 remained unchanged in DDR- and Roc-treated Ewing sarcoma cells (FIG. 7A). As a ubiquitously expressed protein, the EWSR1 levels were also not affected in other types of sarcoma cells treated with rocaglamides (FIGS. 7B-C). In contrast, the levels of the epigenetic modulator LSD1, protein needed for optimal activity of the EWS-FLI1 transcriptional complex (Sankar et al., Oncogene, 32:5089-5100 (2013)), and a key EWS-FLI1 downstream target NKX2.2, a homeobox transcription factor implicated in development, were diminished by DDR and Roc treatment (FIG. 7). Upon inspection of the 5'UTRs for these genes, the inventors noted that the EWSR1 transcript has a very short 5' UTR, while the mRNAs for NKX2.2 and LSD1/KDA 11A contain longer G+C-rich 5'UTRs. Therefore, they hypothesize that the NKX2.2 and LSD1/KDM1A transcripts are eIF4A-dependent.

Intriguingly, prior to caspase activation, Roc- and DDR-treated MPNST cells exhibited increased γH2A.X, a marker of DNA damage response, suggesting that DNA damage may be a key underlying cause of the apoptosis seen at later time points. Roc may affect prohibitin-mediated ERK activation, cause the disruption of mitochondrial integrity, and promote the generation of reactive oxygen species. Callahan et al., Leukemia, 28:1960-1968 (2014). It is possible that rocaglamides induce DNA damage through one or more of these mechanisms. Alternatively, Roc and DDR may affect the translation of proteins responsible for DNA replication and repair,

What is claimed is:

1. A method of treating cancer in a subject in need thereof, consisting of administering a therapeutically effective amount of a compound according to formula I to the subject:

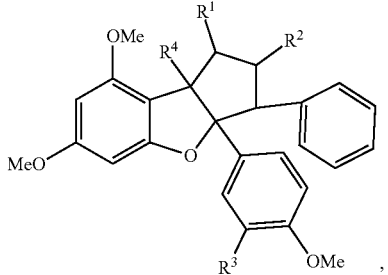

wherein $R^1$ is selected from the group consisting of —OH, —OAc, —OCHO, =O, and =NOH; $R^2$ is selected from the group consisting of —CON(CH$_3$)$_2$, —CONHCH$_3$, —CONH$_2$, —COOCH$_3$, —COOH, and —H, $R^3$ is selected from the group consisting of —H, —OH, and —OCH$_3$, and $R^4$ is selected from the group consisting of —OH, —OCH$_3$, —OCH$_2$CH$_3$, and optionally a pharmaceutically acceptable carrier, wherein the cancer is selected from malignant peripheral nerve sheath tumors, Ewing sarcoma, osteosarcoma, and rhabdomyosarcoma.

2. The method of claim 1, wherein the subject is human.

3. The method of claim 2, wherein the subject is a child.

4. The method of claim 1, wherein the compound is administered together with a pharmaceutically acceptable carrier.

5. The method of claim 2, wherein the cancer is a malignant peripheral nerve sheath tumor.

6. The method of claim 1, wherein $R^4$ is —OH.

7. The method of claim 1, wherein $R^3$ is —H.

8. The method of claim 1, wherein $R^1$ is —OH.

9. The method of claim 1, wherein $R^2$ is —CON(CH$_3$)$_2$, —CONHCH$_3$, or —CONH$_2$.

10. The method of claim 1, wherein the compound is rocaglamide.

11. The method of claim 1, wherein the compound is didesmethylrocaglamide.

12. The method of claim 1, wherein the compound is not sensitive to MDR1 inhibition.

13. The method of claim 1, wherein the compound provided an oral bioavailability of at least about 50%.

* * * * *